US011751567B2

(12) United States Patent
Shi et al.

(10) Patent No.: US 11,751,567 B2
(45) Date of Patent: Sep. 12, 2023

(54) STEROIDAL PIPERIDONE DERIVATIVE, SYNTHESIS METHOD, AND USE THEREOF

(71) Applicant: NORTHWEST A&F UNIVERSITY, Xianyang (CN)

(72) Inventors: Baojun Shi, Xianyang (CN); Weiqi Jiang, Xianyang (CN); Shichuang Ma, Xianyang (CN); Yuxiao Hu, Xianyang (CN); Qiangping Wang, Xianyang (CN)

( * ) Notice: Subject to any disclaimer, the term of this patent is extended or adjusted under 35 U.S.C. 154(b) by 0 days.

(21) Appl. No.: 17/951,129

(22) Filed: Sep. 23, 2022

(65) Prior Publication Data

US 2023/0105315 A1 Apr. 6, 2023

(30) Foreign Application Priority Data

Sep. 23, 2021 (CN) .......................... 202111114215.2

(51) Int. Cl.
*A01N 43/42* (2006.01)
*A01P 7/04* (2006.01)
*C07J 73/00* (2006.01)

(52) U.S. Cl.
CPC ................ *A01N 43/42* (2013.01); *A01P 7/04* (2021.08); *C07J 73/005* (2013.01)

(58) Field of Classification Search
CPC ...................................................... C07J 73/005
See application file for complete search history.

(56) References Cited

PUBLICATIONS

Sumanas Rakhit, et al., N. M. R. Spectra of Some 17-Azasteroids, Steroids, 1967, pp. 135-141, vol. 9 No.2.

*Primary Examiner* — Barbara P Badio

(57) ABSTRACT

A steroidal piperidone derivative, a synthesis method, and a use thereof are provided. The steroidal piperidone derivative has a chemical structure shown in general formula (1) or general formula (2), where R is any one selected from the group consisting of alkyl, phenyl, substituted phenyl, and a heterocycle. In the synthesis method of the steroidal piperidone derivative, dehydroepiandrosterone (DHEA) is used as a basic raw material to prepare the steroidal piperidone derivative of the present disclosure through a series of reactions. A product prepared by the synthesis method has a high yield and is easily separated, and thus the synthesis method is the optimal method for preparing the steroidal piperidone derivative of the present disclosure. The present steroidal piperidone derivative exhibits prominent toxic activity against sucking pests, such as aphids, spider mites, rice planthoppers, and *B. tabaci*, and can be used for the control of a plant pest.

(1)

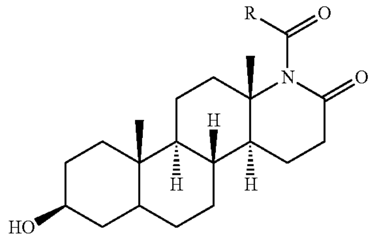

(2)

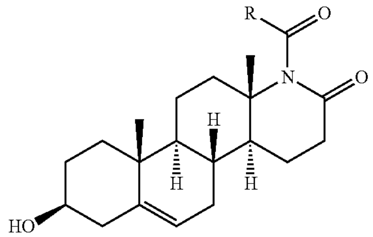

9 Claims, 1 Drawing Sheet

STEROIDAL PIPERIDONE DERIVATIVE, SYNTHESIS METHOD, AND USE THEREOF

CROSS REFERENCE TO THE RELATED APPLICATIONS

This application is based upon and claims priority to Chinese Patent Application No: 202111114215.2, filed on Sep. 23, 2021, the entire contents of which are incorporated herein by reference.

TECHNICAL FIELD

The present disclosure belongs to the technical field of drug synthesis and, in particular, relates to a steroidal piperidone derivative, a synthesis method, and a use thereof.

BACKGROUND

Heterocyclic compounds are ubiquitous in nature, are extensively used, and play a very important role in people's lives. Most drugs and more than half of organic compounds are heterocyclic compounds. The synthesis of heterocyclic compounds and the exploration of their biological activities are important research fields in organic chemistry, medicinal chemistry, and pesticide development. In particular, some heterocyclic compounds with a heteroatom N or O exhibit prominent bactericidal activity and thus have been widely used in pesticides, medicine, and other fields.

Piperidone compounds with nitrogen-containing heterocycles are one of the active fields of research and development in recent years due to their broad-spectrum biological activities and can be mainly used as anticancer, anti-inflammatory, and antipyretic drugs in the medical field and as herbicides, antibacterial agents, plant growth regulators (PGRs), insecticides in the pesticide field. In addition, these compounds can be used as important organic synthesis intermediates.

Sucking pests, such as aphids, whiteflies, rice planthoppers, and mites, are one of the main pests that are harmful to most crops in agriculture. However, with the long-term and frequent use of control agents, the pests become resistant to the control agents. By using heterocyclic compounds and piperidones in pesticides, a series of steroidal piperidone derivatives are synthesized to prepare prominent insecticides.

SUMMARY

A first objective of the present disclosure is to overcome the shortcomings of the prior art and provide a series of steroidal piperidone derivatives with novel structures.

A second objective of the present disclosure is to provide a high-yield synthesis method of the steroidal piperidone derivative.

A third objective of the present disclosure is to provide a use of the steroidal piperidone derivative in the control of a plant pest.

The objectives of the present disclosure are achieved through the following technical solutions: A steroidal piperidone derivative with at least one chemical structure shown in general formula (1) or general formula (2) is provided,

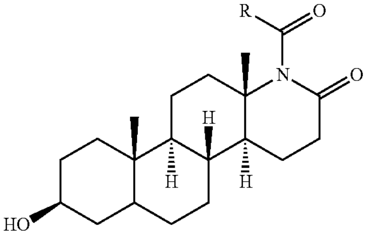
(1)

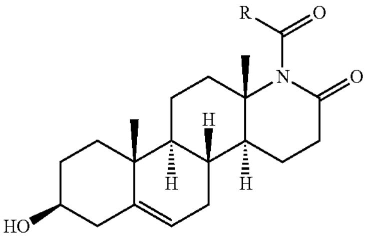
(2)

where R in the chemical structure is any one selected from the group consisting of alkyl, phenyl, substituted phenyl, and a heterocycle, and the alkyl is an aliphatic chain.

Further, R is any one selected from the group consisting of (1 g) to (6 g):

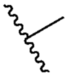
(1g)

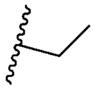
(2g)

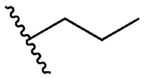
(3g)

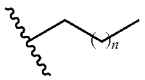
(4g)

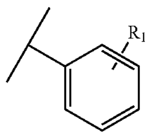
(5g)

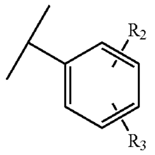
(6g)

where n=1, 2, 3, 4, . . . n;

$R_1$ is a substituent at an ortho, meta, or para position;

$R_2$ and $R_3$ are each 2,3-substituted, 2,4-substituted, 2,5-substituted, 2,6-substituted, 3,4-substituted, 3,5-substituted, 3,6-substituted, 4,5-substituted, 4,6-substituted, or 5,6-substituted; and substituents of $R_1$, $R_2$, and $R_3$ are each any one selected from the group consisting of halogen, trifluoromethyl, methyl, nitro, and methoxy. The halogen represents fluorine, chlorine, bromine, or iodine; the trifluoromethyl represents a group of —$CF_3$; methyl represents a group of —$CH_3$; the nitro represents a group of —$NO_2$; and the methoxy represents a group of —$OCH_3$.
Further, the steroidal piperidone derivative has the following chemical structure:
(1)-1
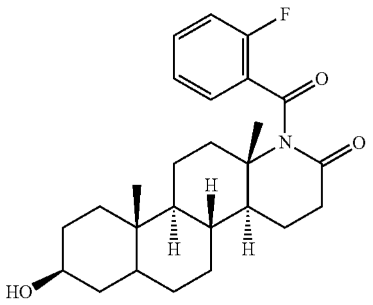
(1)-2
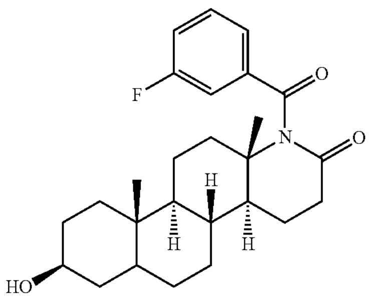
(1)-3
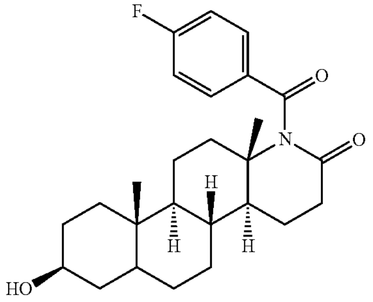
(1)-4
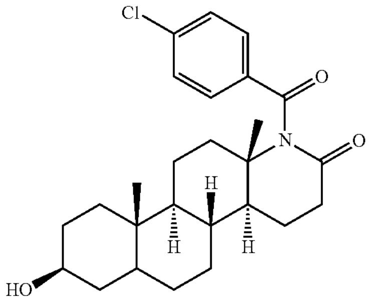
-continued
(1)-5
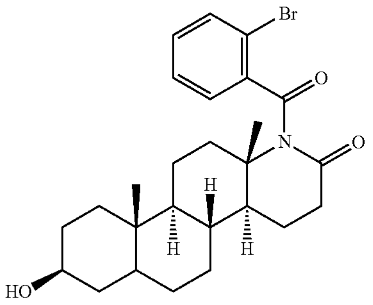
(1)-6
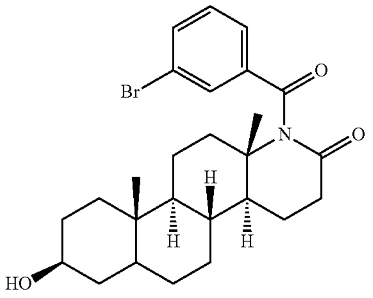
(1)-7
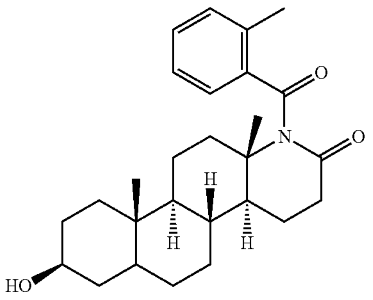
(1)-8
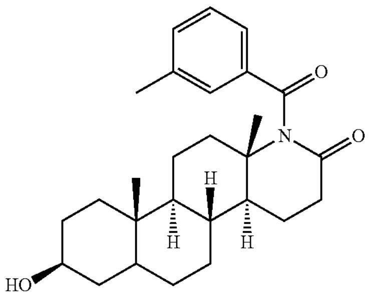
(1)-9
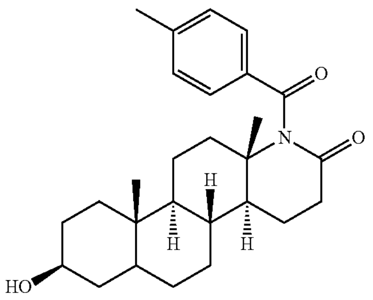

-continued
(1)-10
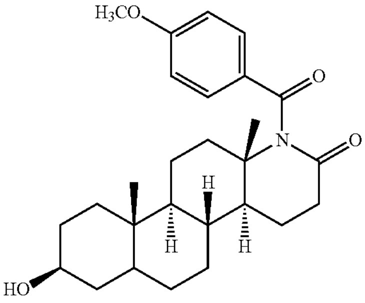
(1)-11
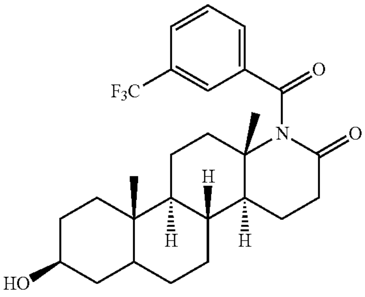
(1)-12
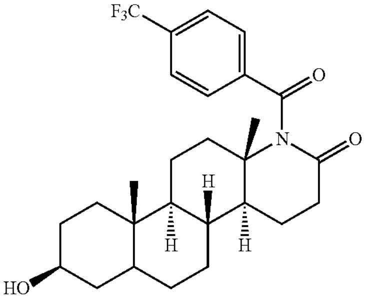
(1)-13
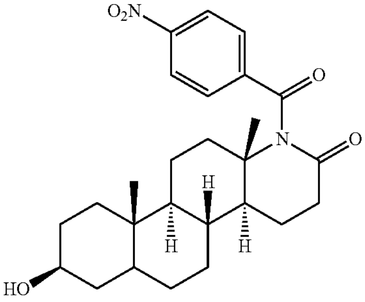
(2)-1
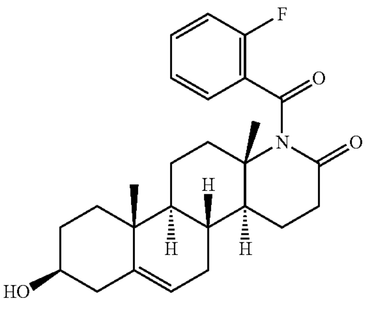
-continued
(2)-2
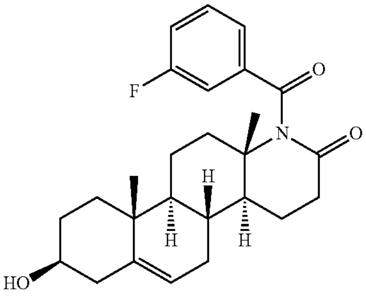
(2)-3
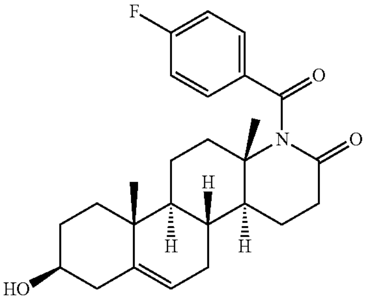
(2)-4
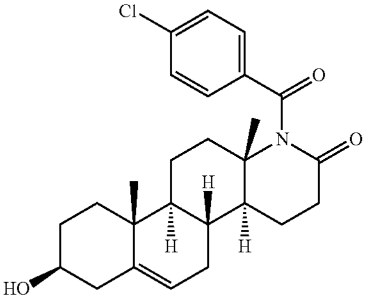
(2)-5
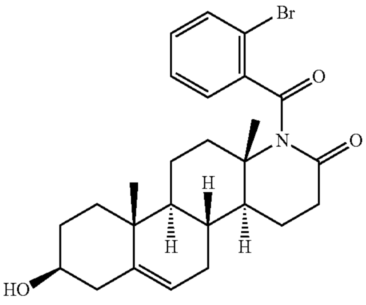
(2)-6
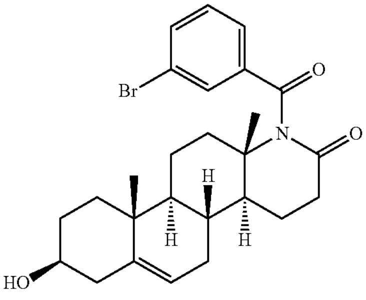

-continued
(2)-7
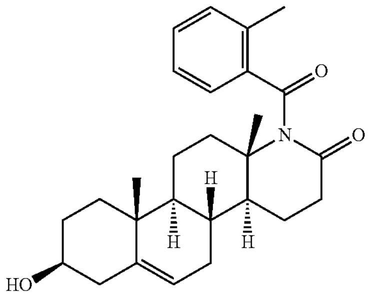
(2)-8
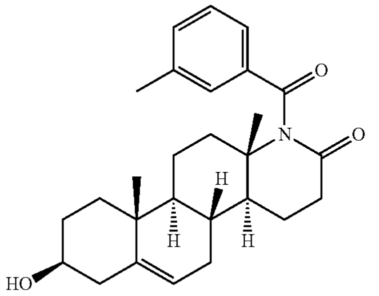
(2)-9
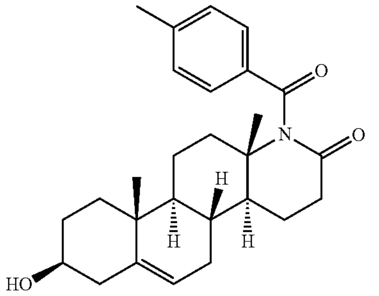
(2)-10
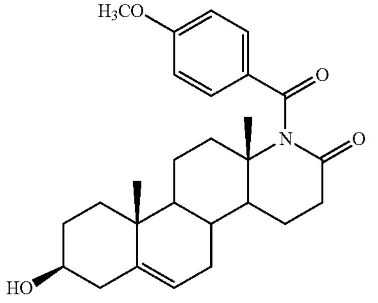
(2)-11
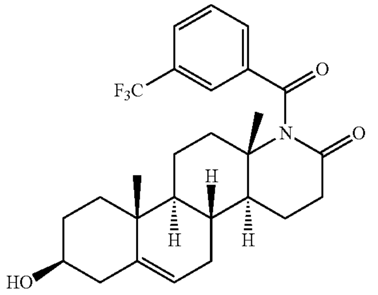
-continued
(2)-12
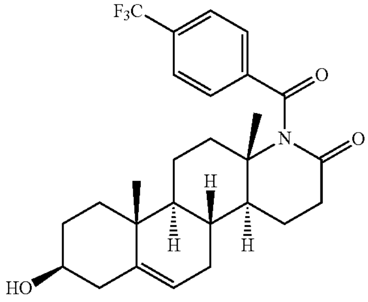
(2)-13
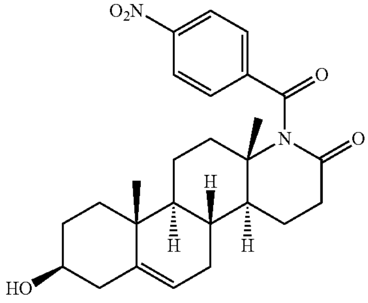
A synthesis method of the steroidal piperidone derivative is provided, including the following synthetic route:
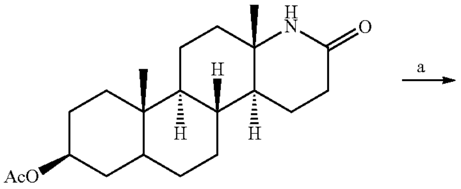
(3)
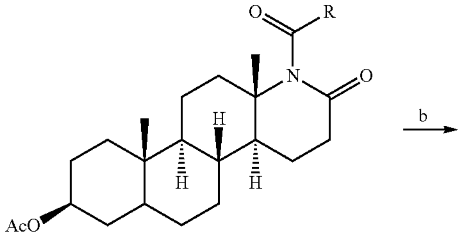
(4)
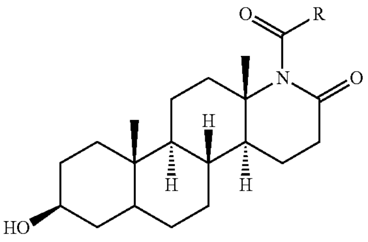
(1)

-continued

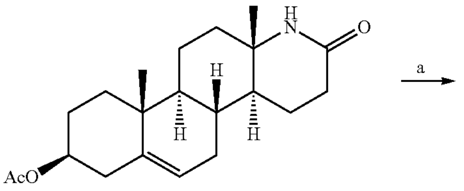

(5)

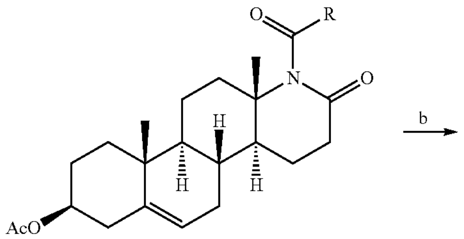

(6)

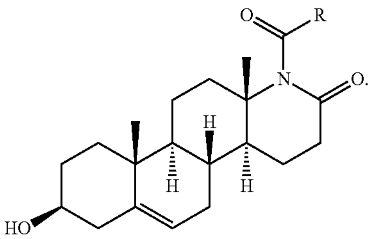

(2)

Further, step a is conducted as follows: adding 4-dimethylaminopyridine, triethylamine (TEA), and an acyl chloride with various substituents successively to dichloromethane (DCM) in which a compound (3) or (5) is dissolved, and conducting a reaction at room temperature for 6 h. Step b is conducted as follows: with methanol as a solvent, adding sodium carbonate, and conducting a reaction under reflux for 2 h.

Further, synthetic routes of the compounds (3) and (5) are as follows:

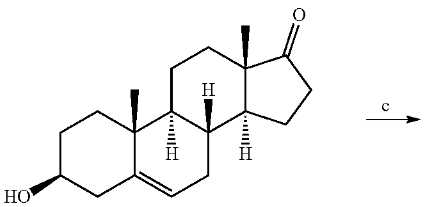

(7)

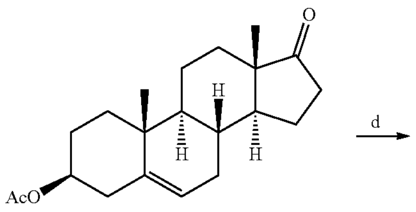

(8)

-continued

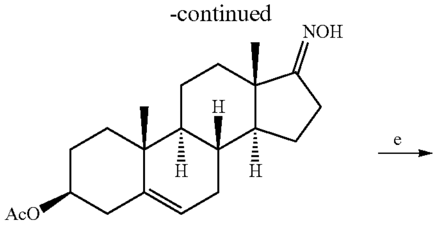

(9)

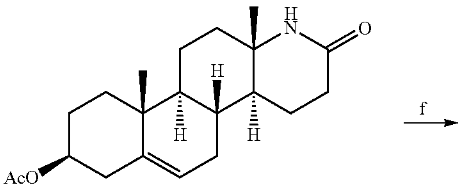

(5)

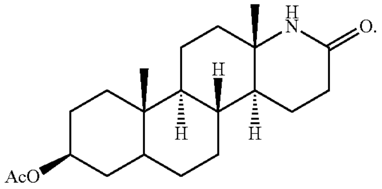

(3)

Further, step c is conducted as follows: adding acetic anhydride to a solution of a compound (7) in DCM, adding 4-dimethylaminopyridine and TEA, and conducting a reaction at 25° C. for 2 h.

Step d is conducted as follows: with ethanol as a solvent, adding a compound (8), hydroxylamine hydrochloride, and sodium acetate, and conducting a reaction at room temperature for 0.5 h.

Step e is conducted as follows: with tetrahydrofuran (THF) as a solvent, adding thionyl chloride, and conducting a reaction at room temperature for 1 h.

Step f is conducted as follows: with ethanol as a solvent and Pb/C as a catalyst, introducing hydrogen, and conducting a reaction at room temperature for 60 h.

A use of the steroidal piperidone derivative in the control of a plant pest is provided.

Further, the plant pest is a sucking pest. The steroidal piperidone derivative can be specifically used for the control of aphids, whiteflies, rice planthoppers, and spider mites.

An insecticide prepared from the steroidal piperidone derivative is provided.

Further, the effective content of the steroidal piperidone derivative in the insecticide is 0.01% to 99.99%.

To use the steroidal piperidone derivative in the fields of agriculture and plant protection, those of ordinary skill in the art can use one or more of the steroidal piperidone derivatives as insecticidal active ingredients in combination with a pesticidal acceptable carrier or another agricultural active ingredient to prepare a formulation for easy application, which has a dosage form, such as a water dispersible granule (WDG), a wettable powder (WP), or a dispersible oil suspension. When the above-mentioned different dosage forms are prepared, in addition to the selected bactericidal active ingredient, those of ordinary skill in the art need to adopt a variety of adjuvants. Different auxiliary ingredients (adjuvants) for pesticide formulations can be selected and used according to needs. The auxiliary ingredient can be one or more selected from the group consisting of a dispersing medium, a dispersing agent, an emulsifying agent, a wetting agent, a thickening agent, a defoaming agent, an anti-freezing agent, a disintegrating agent, a binder, and a filler.

The present disclosure has the following advantages:

(1) The present disclosure provides a series of brand-new steroidal piperidone derivatives for the first time. In addition, the present disclosure also provides a synthesis method of the steroidal piperidone derivative. In the synthesis method, dehydroepiandrosterone (DHEA) is used as a basic raw material to prepare the steroidal piperidone derivative of the present disclosure through a series of reactions. A product prepared by the synthesis method has a high yield and is easily separated, and thus the synthesis method is the optimal method for preparing the steroidal piperidone derivative of the present disclosure.

(2) It has been confirmed by bioassays that the steroidal piperidone derivative provided by the present disclosure exhibits prominent toxic activity against sucking pests, such as aphids, spider mites, rice planthoppers, and whiteflies, and can be used for the control of a plant pest.

DETAILED DESCRIPTION OF THE EMBODIMENTS

Figure 1:
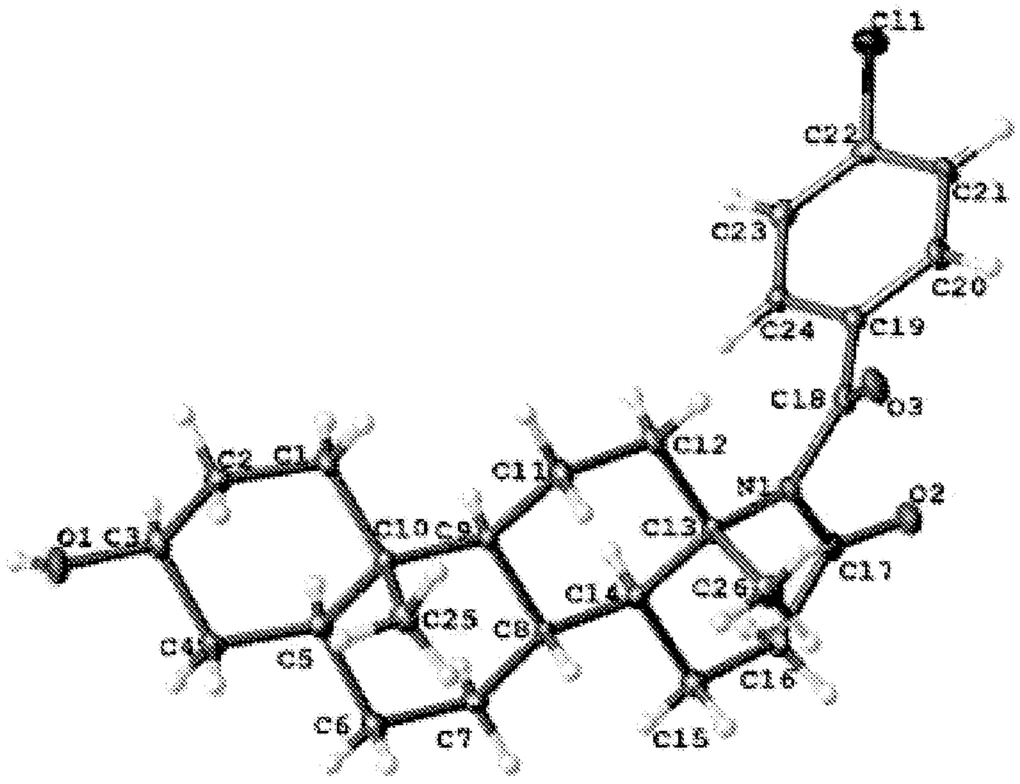
FIG. 1 is a schematic diagram of single-crystal diffraction of the compound (1)-6 in the present disclosure.

The present disclosure is further described below in conjunction with the accompanying drawings and specific examples, but the protection scope of the present disclosure is not limited thereto.

A steroidal piperidone derivative with a chemical structure shown in general formula (1) or general formula (2) is provided, (1)

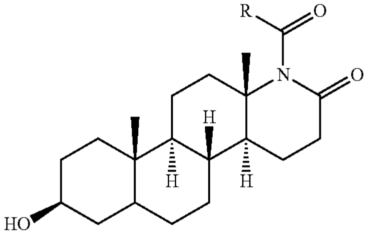

(2)

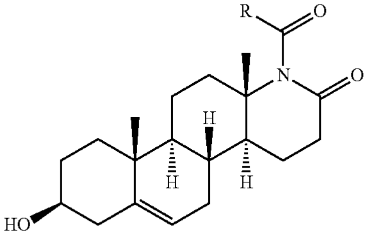

where R in the chemical structure is any one selected from the group consisting of alkyl, phenyl, substituted phenyl, and a heterocycle, and the alkyl is an aliphatic chain.

A synthetic route of the steroidal piperidone derivative of the present disclosure is as follows:

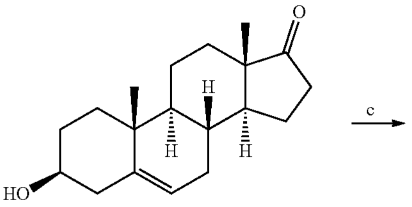

(7)

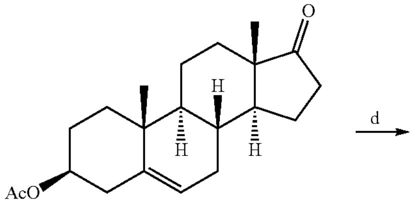

(8)

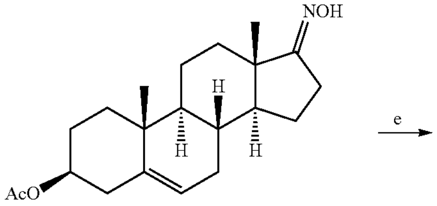

(9)

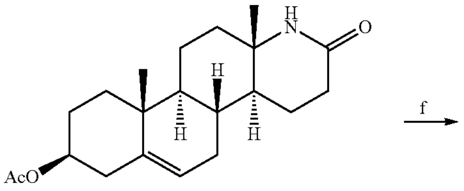

(5)

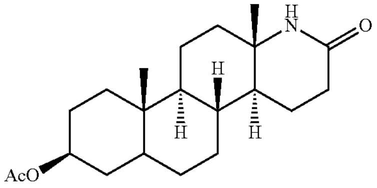

(3)

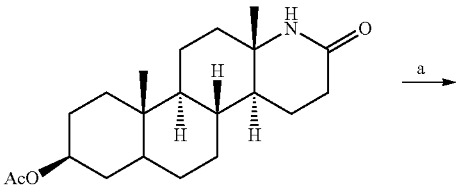

(3)

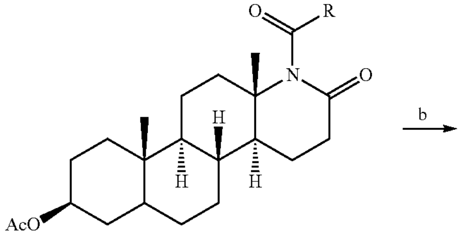

(4)

-continued

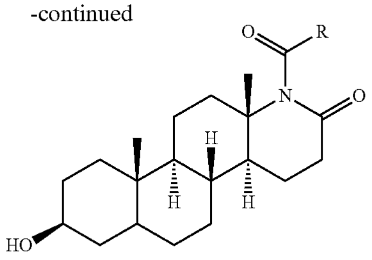

(1)

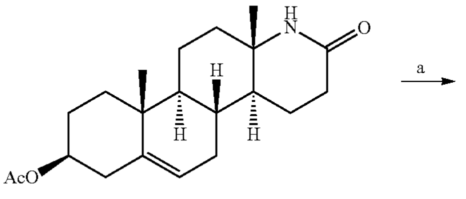

(5)

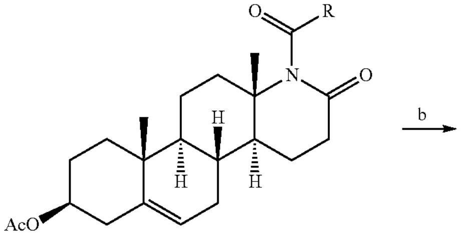

(6)

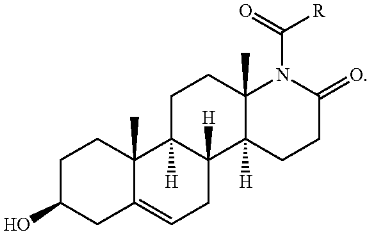

(2)

1. DHEA (7) is allowed to react with acetic anhydride, 4-dimethylaminopyridine, and TEA to protect 3-hydroxyl of DHEA (7). Sodium acetate and hydroxylamine hydrochloride are added with ethanol as a solvent to obtain a compound (9). A compound (5) is prepared in the presence of thionyl chloride. A compound (3) is prepared with ethanol as a solvent and Pb/C as a catalyst.

2. The compound (3) or (5) is used as a reaction raw material. TEA and 4-dimethylaminopyridine are added with DCM as a solvent to obtain a compound (4) or (6). Sodium carbonate is added with methanol as a solvent to obtain a compound (1) or (2).

Reaction reagents and conditions in each step of the above-mentioned synthetic route are as follows:

step a: DMAP, $Et_3N$, DCM, 0° C.;

step b: $Na_2CO_3$, MeOH, 70° C.;

step c: $Ac_2O$, DMAP, $Et_3N$, 25° C.;

step d: $NH_2OH{\cdot}HCl$, $CH_3COONa$, EtOH, 80° C.;

step e: $SOCl_2$, THF, 0° C.;

step f: Pb/C, $H_2$, 25° C.

Example 1

Synthesis Method of a Steroidal Piperidone Derivative (1) 4.33 g of DHEA (15 mmol) was added to 40 mL of DCM in a dry round-bottomed flask. The resulting mixture was stirred until DHEA was completely dissolved. 2.24 g of acetic anhydride (22 mmol), 0.012 g of 4-dimethylamino-pyridine (0.1 mmol), and 4.04 g of TEA (20 mmol) were successively added, and the reaction was conducted at room temperature for 2 h. Water and DCM were added for extraction, and the resulting organic phase was dried over anhydrous sodium sulfate and subjected to vacuum concentration to obtain 4.86 g of a white solid compound (8). 4.95 g of the compound (8) (15 mmol) was dissolved in 50 mL of ethanol. 2.90 g of hydroxylamine hydrochloride (45 mmol) and 3.69 g of sodium acetate (45 mmol) were successively added, and the reaction was conducted at room temperature for 0.5 h. Vacuum concentration was conducted to remove the organic layer, and filtration was conducted with ice water to obtain 5.08 g of a white solid compound (9). In the synthesis of piperidone, 3.45 g of the compound (9) (10 mmol) was dissolved in 15 mL of THF, 2.38 g of thionyl chloride (20 mmol) was added, the resulting mixture was stirred at room temperature for 1 h, and the pH was adjusted to higher than 7.0 with ammonium hydroxide to obtain 1.73 g of a white solid compound (5).

(2) 3.45 g of the compound (5) (10 mmol) was dissolved in 40 mL of an ethanol solution. 0.532 g of Pb/C (5%) was added as a catalyst. The reaction was conducted at room temperature for 60 h under the protection of hydrogen. The resulting reaction solution was filtered, and a filtrate was subjected to vacuum distillation to obtain 2.25 g of a white solid compound (3).

(3) 0.35 g of the compound (3) or (5) (1 mmol), 0.06 g of 4-dimethylaminopyridine (0.5 mmol), 0.30 g of TEA (3 mmol), and a mixture of corresponding acyl chlorides (2 mmol) were successively added to 10 mL of DCM, and the resulting mixture was stirred at 0° C. for 4 h. After the reaction was complete, DCM and a 1 mol/L hydrochloric acid aqueous solution were added for extraction, and purification was conducted with petroleum ether and ethyl acetate in 4:1 (v/v) to obtain a white solid compound (4) or (6). With methanol as a solvent, 0.11 g of a sodium carbonate (1 mmol) aqueous solution was added, and the reaction was conducted at 70° C. for 3 h. After the reaction was complete, vacuum concentration was conducted to remove the organic layer, DCM and 1 mol/L hydrochloric acid aqueous solution were added for extraction, and purification was conducted with petroleum ether and ethyl acetate in 4:1 (v/v) to obtain a white solid compound (1) or (2).

Example 2

Figure 2:
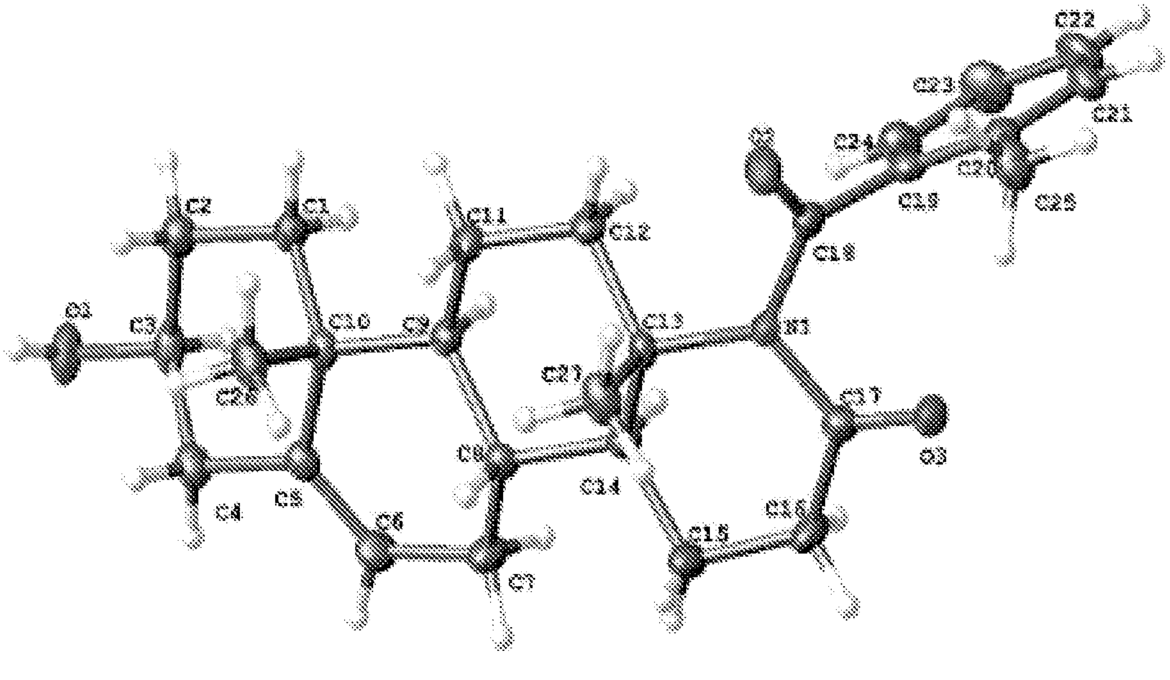
FIG. 2 is a schematic diagram of single-crystal diffraction of the compound (2)-9 in the present disclosure.

The steroidal piperidone derivatives prepared by the above method were confirmed by $^1$H-NMR and $^{13}$C-NMR, and the structures of the compounds (1)-6 and (2)-9 were confirmed by single-crystal diffraction. A schematic diagram of single-crystal diffraction of the compound (1)-6 is shown in FIG. 1, and a schematic diagram of single-crystal diffraction of the compound (2)-9 is shown in FIG. 2. Specific results were as follows:

1. Compound (1)-1:

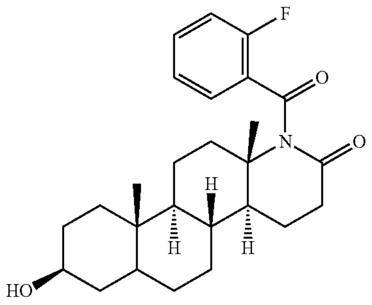

$^1H$ NMR (500 MHz, $CDCl_3$) δ=7.74 (t, J=8.6 Hz, 1H), 7.45-7.40 (m, 1H), 7.19 (t, J=7.6 Hz, 1H), 7.00 (dd, J=11.3, 8.3 Hz, 1H), 3.62-3.56 (m, 1H), 2.60-2.44 (m, 3H), 2.07-2.02 (m, 1H), 1.98-1.93 (m, 1H), 1.82-1.76 (m, 1H), 1.74-1.67 (m, 2H), 1.64 (s, 1H), 1.62-1.57 (m, 2H), 1.50 (s, 3H), 1.41-1.25 (m, 9H), 1.15-1.09 (m, 1H), 1.01-0.93 (m, 2H), 0.79 (s, 3H).

$^{13}C$ NMR (125 MHz, $CDCl_3$) δ=174.08, 171.36, 158.70, 133.65 (d, $J_{CF}$=9.0 Hz), 131.17, 125.66 (d, $J_{CF}$=10.0 Hz), 124.59, 116.27 (d, $J_{CF}$=23.3 Hz), 71.25, 63.19, 53.09, 48.57, 44.30, 37.95, 36.85, 36.28, 36.21, 35.58, 32.56, 31.45, 30.97, 28.57, 21.65, 20.86, 20.02, 12.28.

2. Compound (1)-2:

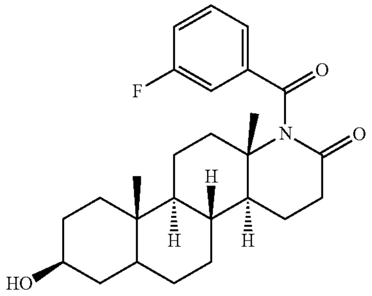

$^1H$ NMR (500 MHz, $CDCl_3$) δ=7.54 (d, J=7.9 Hz, 1H), 7.43-7.35 (m, 2H), 7.21-7.17 (m, 1H), 3.60-3.53 (m, 1H), 2.59-2.49 (m, 2H), 2.21-1.94 (m, 3H), 1.79-1.56 (m, 7H), 1.51 (s, 3H), 1.39-1.13 (m, 9H), 0.99-0.90 (m, 2H), 0.77 (s, 3H).

$^{13}C$ NMR (125 MHz, $CDCl_3$) δ=175.36, 173.70, 162.78 (d, $J_{CF}$=247.2 Hz), 138.45 (d, $J_{CF}$=6.7 Hz), 130.30 (d, $J_{CF}$=7.9 Hz), 124.57 (d, $J_{CF}$=2.8 Hz), 119.83 (d, J $J_{CF}$=21.3 Hz), 115.70 (d, $J_{CF}$=22.9 Hz), 71.11, 62.29, 53.09, 48.26, 44.29, 37.87, 36.81, 36.39, 36.32, 35.56, 32.01, 31.36, 30.90, 28.48, 21.34, 21.03, 20.18, 12.25.

3. Compound (1)-3:

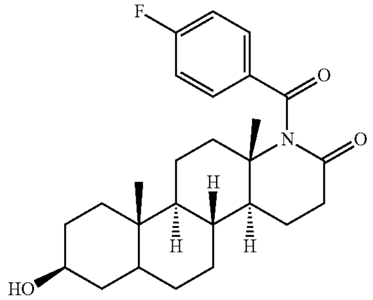

$^1H$ NMR (400 MHz, $CDCl_3$) δ=7.79 (dd, J=8.7, 5.5 Hz, 2H), 7.07 (t, J=8.6 Hz, 2H), 3.60-3.52 (m, 1H), 2.57-2.53 (m, 2H), 2.17-1.93 (m, 3H), 1.78-1.55 (m, 7H), 1.51 (s, 3H), 1.42-1.09 (m, 9H), 0.98-0.79 (m, 3H), 0.77 (s, 3H).

$^{13}C$ NMR (100 MHz, $CDCl_3$) δ=175.21, 173.40, 165.70 (d, $J_{CF}$=253 Hz), 132.37 (d, $J_{CF}$=3.0 Hz), 131.72 (d, $J_{CF}$=10.0 Hz), 115.86 (d, $J_{CF}$=22.0 Hz), 71.11, 62.02, 53.12, 48.25, 44.29, 37.86, 36.80, 36.47, 36.34, 35.56, 31.83, 31.35, 30.90, 28.48, 21.29, 21.15, 20.18, 12.25.

4. Compound (1)-4:

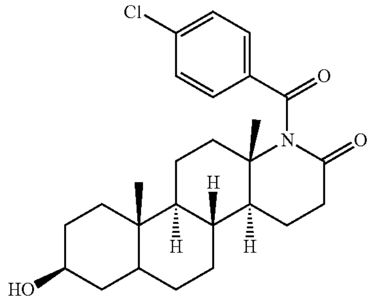

$^1H$ NMR (500 MHz, $CDCl_3$) δ=7.51 (d, J=7.2 Hz, 1H), 7.34-7.27 (m, 3H), 3.63-3.57 (m, 1H), 2.71-2.67 (m, 1H), 2.57-2.49 (m, 2H), 2.07-1.93 (m, 2H), 1.83-1.71 (m, 3H), 1.65-1.58 (m, 3H), 1.52 (s, 3H), 1.50-1.38 (m, 5H), 1.27 (d, J=12.0 Hz, 3H), 1.16-1.10 (m, 1H), 1.01-0.84 (m, 3H), 0.80 (s, 3H).

$^{13}C$ NMR (125 MHz, $CDCl_3$) δ=174.32, 172.87, 137.40, 131.36, 130.93, 130.46, 130.08, 127.01, 71.26, 63.95, 53.15, 48.60, 44.31, 37.96, 36.87, 36.34, 35.84, 35.60, 33.00, 31.49, 31.03, 28.58, 21.80, 20.29, 20.06, 12.29.

5. Compound (1)-5:

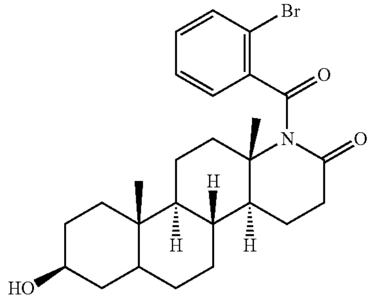

$^{1}H$ NMR (400 MHz, $CDCl_3$) δ=7.53 (d, J=7.9 Hz, 1H), 7.45 (d, J=7.6 Hz, 1H), 7.31 (t, J=7.8 Hz, 1H), 7.21 (t, J=8.6 Hz, 1H), 3.63-3.55 (m, 1H), 2.74-2.69 (m, 1H), 2.56-2.51 (m, 2H), 2.07-1.92 (m, 2H), 1.82-1.55 (m, 7H), 1.52 (s, 3H), 1.44-1.23 (m, 7H), 1.16-1.08 (m, 1H), 1.02-0.84 (m, 3H), 0.79 (s, 3H).

$^{13}C$ NMR (100 MHz, $CDCl_3$) δ 174.44, 173.50, 139.33, 133.79, 131.34, 129.82, 127.45, 119.60, 71.21, 64.06, 53.11, 48.50, 44.26, 37.89, 36.83, 36.30, 35.68, 35.57, 33.09, 31.43, 31.01, 28.54, 21.77, 20.15, 20.06, 12.27.

6. Compound (1)-6:

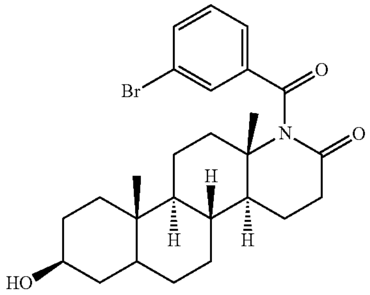

$^{1}H$ NMR (500 MHz, $CDCl_3$) δ=7.85 (t, J=1.9 Hz, 1H), 7.67-7.61 (m, 2H), 7.29 (d, J=7.9 Hz, 1H), 3.62-3.56 (m, 1H), 2.58-2.54 (m, 2H), 2.23-2.20 (m, 1H), 2.11-2.06 (m, 1H), 1.99-1.95 (m, 1H), 1.82-1.78 (m, 1H), 1.72-1.57 (m, 6H), 1.52 (s, 3H), 1.41-1.14 (m, 9H), 1.02-0.92 (m, 2H), 0.79 (s, 3H).

$^{13}C$ NMR (125 MHz, $CDCl_3$) δ 175.20, 173.77, 138.28, 135.68, 131.70, 130.26, 127.47, 122.83, 71.22, 62.41, 53.09, 48.30, 44.33, 37.94, 36.84, 36.43, 36.37, 35.61, 32.11, 31.44, 30.94, 28.53, 21.40, 21.03, 20.23, 12.29.

7. Compound (1)-7:

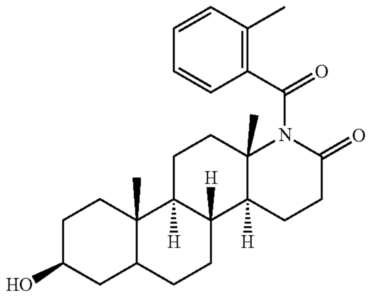

$^{1}H$ NMR (400 MHz, $CDCl_3$) δ 7.60 (s, 1H), 7.54 (d, J=7.5 Hz, 1H), 7.33-7.28 (m, 2H), 3.60-3.52 (m, 1H), 2.62-2.49 (m, 2H), 2.38 (s, 3H), 2.18-1.94 (m, 3H), 1.79-1.55 (m, 7H), 1.52 (s, 3H), 1.42-1.13 (m, 8H), 1.07-0.82 (m, 3H), 0.78 (s, 3H).

$^{13}C$ NMR (100 MHz, $CDCl_3$) δ176.65, 173.34, 138.50, 136.06, 133.88, 129.55, 128.54, 126.32, 71.13, 61.87, 53.09, 48.17, 44.30, 37.88, 36.80, 36.39, 36.33, 35.56, 31.87, 31.37, 30.90, 28.51, 21.48, 21.31, 21.17, 20.24, 12.25.

8. Compound (1)-8:

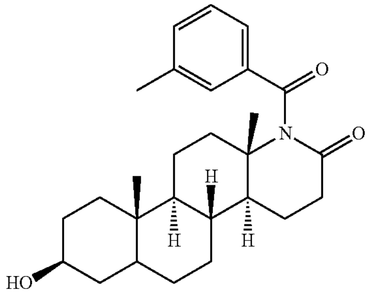

$^{1}H$ NMR (500 MHz, $CDCl_3$) δ=7.61 (s, 1H), 7.55 (d, J=7.5 Hz, 1H), 7.33-7.28 (m, 2H), 3.62-3.55 (m, 1H), 2.60-2.50 (m, 2H), 2.38 (s, 3H), 2.19-1.96 (m, 3H), 1.82-1.77 (m, 1H), 1.63-1.59 (m, 4H), 1.53 (s, 3H), 1.45-1.36 (m, 4H), 1.31-1.21 (m, 8H), 0.98-0.90 (m, 2H), 0.79 (s, 3H).

$^{13}C$ NMR (125 MHz, $CDCl_3$) δ=176.69, 173.34, 138.55, 136.17, 133.89, 129.60, 128.58, 126.36, 71.26, 61.91, 53.19, 48.27, 44.39, 37.99, 36.88, 36.47, 36.42, 35.63, 31.95, 31.48, 30.97, 28.57, 21.52, 21.38, 21.20, 20.32, 12.30.

9. Compound (1)-9:

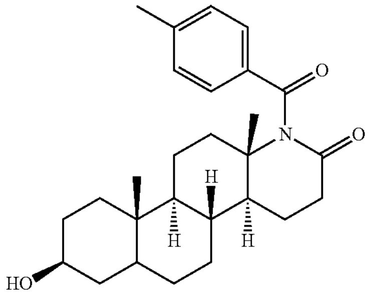

$^{1}H$ NMR (500 MHz, $CDCl_3$) δ 7.69 (d, J=7.9 Hz, 2H), 7.20 (d, J=7.9 Hz, 2H), 3.60-3.54 (m, 1H), 2.57-2.53 (m, 2H), 2.37 (s, 3H), 2.15-2.04 (m, 2H), 1.99-1.94 (m, 1H), 1.79-1.64 (m, 3H), 1.61-1.56 (m, 4H), 1.52 (s, 3H), 1.41-1.01 (m, 9H), 0.96-0.86 (m, 2H), 0.77 (s, 3H).

$^{13}C$ NMR (125 MHz, $CDCl_3$) δ 176.27, 173.16, 143.97, 133.36, 129.46, 129.38, 71.17, 61.73, 53.16, 48.20, 44.33, 37.91, 36.83, 36.47, 36.37, 35.57, 31.78, 31.40, 30.93, 28.52, 21.78, 21.30, 21.23, 20.25, 12.27.

10. Compound (1)-10:

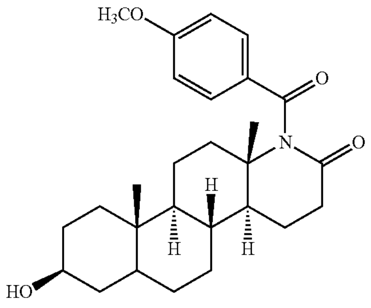

$^{1}H$ NMR (500 MHz, $CDCl_3$) δ=7.78 (d, J=8.4 Hz, 2H), 6.90 (d, J=8.4 Hz, 2H), 3.84 (s, 3H), 3.62-3.55 (m, 1H), 2.58-2.55 (m, 2H), 2.11-2.04 (m, 2H), 1.99-1.95 (m, 1H), 1.79 (d, J=13.0 Hz, 1H), 1.64-1.58 (m, 6H), 1.52 (s, 3H), 1.32-1.25 (m, 7H), 0.99-0.84 (m, 4H), 0.78 (s, 3H).

$^{13}C$ NMR (125 MHz, $CDCl_3$) δ=175.50, 172.89, 163.77, 131.83, 128.50, 114.07, 71.26, 61.55, 55.64, 53.22, 48.23, 44.38, 37.97, 36.86, 36.58, 36.44, 35.61, 31.65, 31.45, 30.96, 28.55, 21.33, 21.30, 20.29, 12.30.

11. Compound (1)-11:

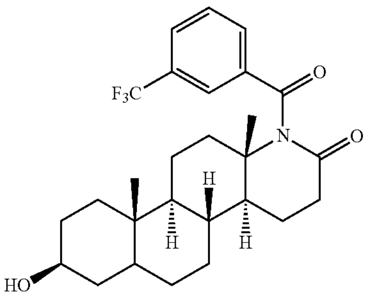

$^1H$ NMR (500 MHz, $CDCl_3$) δ 7.98 (s, 1H), 7.89 (d, J=7.8 Hz, 1H), 7.74 (d, J=7.7 Hz, 1H), 7.53 (t, J=7.8 Hz, 1H), 3.61-3.55 (m, 1H), 2.58-2.53 (m, 2H), 2.26-2.23 (m, 1H), 2.12-2.07 (m, 1H), 1.99-1.95 (m, 1H), 1.71-1.58 (m, 6H), 1.54 (s, 3H), 1.42-1.37 (m, 3H), 1.26 (q, J=11.2 Hz, 5H), 1.12-0.83 (m, 4H), 0.79 (s, 3H).

$^{13}C$ NMR (125 MHz, $CDCl_3$) δ 175.24, 173.93, 137.17, 131.95, 131.30 (d, $J_{CF}$=32.9 Hz), 129.33, 129.18, 125.52 (d, $J_{CF}$=4.0 Hz), 123.77 (d, $J_{CF}$=272.5 Hz), 71.17, 62.58, 53.09, 48.39, 44.31, 37.91, 36.83, 36.48, 36.36, 35.60, 32.16, 31.41, 30.92, 28.51, 21.40, 20.98, 20.20, 12.27.

12. Compound (1)-12:

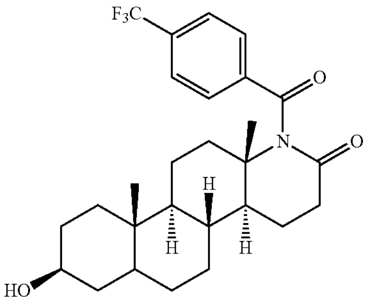

$^1H$ NMR (400 MHz, $CDCl_3$) δ 7.83 (d, J=8.1 Hz, 2H), 7.65 (d, J=8.1 Hz, 2H), 3.60-3.52 (m, 1H), 2.57-2.53 (m, 2H), 2.27-2.24 (m, 1H), 2.12-2.05 (m, 1H), 2.00-1.94 (m, 1H), 1.77-1.56 (m, 7H), 1.53 (s, 3H), 1.42-1.22 (m, 8H), 1.11-0.92 (m, 3H), 0.78 (s, 3H).

$^{13}C$ NMR (100 MHz, $CDCl_3$) δ 175.39, 173.96, 133.91 (q, $J_{CF}$=32.8 Hz), 128.95, 125.75 (q, $J_{CF}$=3.8 Hz), 125.05, 122.34, 71.08, 62.56, 53.10, 48.37, 44.27, 37.83, 36.79, 36.41, 36.29, 35.55, 32.14, 31.33, 30.91, 28.46, 21.37, 20.93, 20.11, 12.23.

13. Compound (1)-13:

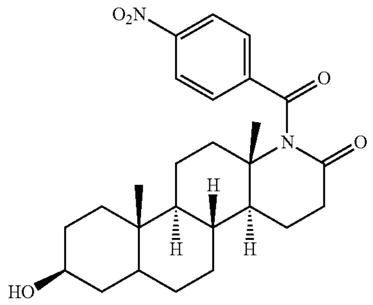

$^1H$ NMR (400 MHz, $CDCl_3$) δ 8.24 (d, J=8.8 Hz, 2H), 7.83 (d, J=8.8 Hz, 2H), 3.63-3.55 (m, 1H), 2.58-2.54 (m, 2H), 2.36-2.32 (m, 1H), 2.14-2.07 (m, 1H), 2.01-1.95 (m, 1H), 1.82-1.58 (m, 7H), 1.54 (s, 3H), 1.45-1.38 (m, 3H), 1.28-1.24 (m, 4H), 1.16-0.92 (m, 4H), 0.80 (s, 3H).

$^{13}C$ NMR (100 MHz, $CDCl_3$) δ 174.74, 174.26, 149.87, 141.95, 129.30, 123.96, 71.18, 63.00, 53.13, 48.53, 44.31, 37.90, 36.85, 36.46, 36.34, 35.60, 32.40, 31.41, 30.97, 28.49, 21.48, 20.79, 20.12, 12.29.

14. Compound (2)-1:

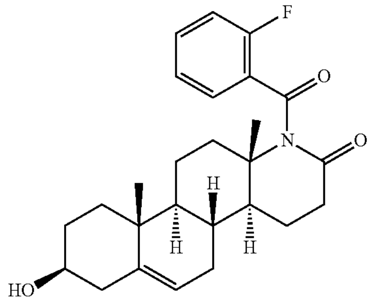

$^1H$ NMR (400 MHz, $CDCl_3$) δ=7.74-7.70 (m, 1H), 7.43-7.37 (m, 1H), 7.17 (t, J=7.4 Hz, 1H), 6.98 (dd, J=11.3, 8.2 Hz, 1H), 5.35-5.32 (m, 1H), 3.50-3.42 (m, 1H), 2.57-2.43 (m, 3H), 2.31-2.14 (m, 4H), 2.02-1.94 (m, 1H), 1.83-1.55 (m, 6H), 1.50 (s, 3H), 1.47-1.23 (m, 4H), 1.14-1.01 (m, 2H), 0.96 (s, 3H).

$^{13}C$ NMR (100 MHz, $CDCl_3$) δ=174.00, 171.22 (d, $J_{CF}$=2.1 Hz), 159.83 (d, $J_{CF}$=254.0 Hz), 140.80, 133.60 (d, $J_{CF}$=9.1 Hz), 131.01, 125.46 (d, $J_{CF}$=10.1 Hz), 124.48 (d, $J_{CF}$=3.5 Hz), 120.60, 116.17 (d, $J_{CF}$=23.0 Hz), 71.37, 62.82, 48.79, 48.77, 41.82, 36.90, 36.59, 35.52, 32.78, 32.59, 31.44, 31.39, 21.31, 20.77, 20.06, 19.21.

15. Compound (2)-2:

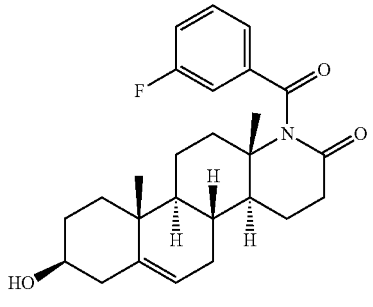

$^1$H NMR (400 MHz, $CDCl_3$) δ=7.53 (dd, J=7.8, 1.4 Hz, 1H), 7.44-7.34 (m, 2H), 7.22-7.17 (m, 1H), 5.38-5.35 (m, 1H), 3.53-3.46 (m, 1H), 2.60-2.55 (m, 2H), 2.34-2.16 (m, 4H), 2.06-2.00 m, 1H), 1.83-1.79 (m, 3H), 1.71-1.58 (m, 4H), 1.54 (s, 3H), 1.50-1.24 (m, 4H), 1.15-1.01 (m, 2H), 0.98 (s, 3H).

$^{13}$C NMR (100 MHz, $CDCl_3$) δ=175.35 (d, $J_{CF}$=2.9 Hz), 173.70, 162.76 (d, $J_{CF}$=247.2 Hz), 140.79, 138.41 (d, $J_{CF}$=6.9 Hz), 130.31 (d, $J_{CF}$=7.7 Hz), 124.53 (d, $J_{CF}$=2.9 Hz), 120.67, 119.86 (d, $J_{CF}$=21.4 Hz), 115.68 (d, $J_{CF}$=22.9 Hz), 71.50, 62.04, 48.88, 48.64, 41.91, 36.95, 36.66, 35.86, 32.88, 32.20, 31.47, 31.46, 21.11, 21.02, 20.35, 19.28.

16. Compound (2)-3:

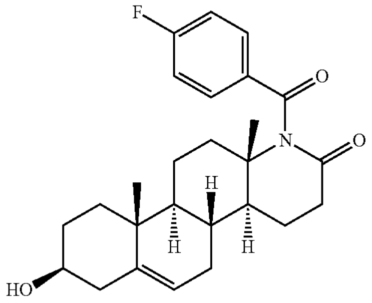

$^1$H NMR (500 MHz, $CDCl_3$) δ=7.81-7.78 (m, 2H), 7.07 (t, J=8.3 Hz, 2H), 5.38-5.37 (m, 1H), 3.54-3.48 (m, 1H), 2.59-2.56 (m, 2H), 2.34-2.17 (m, 4H), 2.05-2.01 (m, 1H), 1.84-1.80 (m, 2H), 1.72-1.58 (m, 6H), 1.55 (s, 3H), 1.45-1.25 (m, 3H), 1.14-1.02 (m, 2H), 0.98 (s, 3H).

$^{13}$C NMR (125 MHz, $CDCl_3$) δ=175.23, 173.37, 165.72 (d, $J_{CF}$=254.6 Hz), 140.82, 132.42, 131.70 (d, $J_{CF}$=9.4 Hz), 120.73, 115.89 (d, $J_{CF}$=22.2 Hz), 71.60, 61.81, 49.00, 48.73, 41.99, 37.01, 36.72, 36.02, 32.98, 32.09, 31.56, 31.52, 21.16, 21.13, 20.43, 19.32.

17. Compound (2)-4:

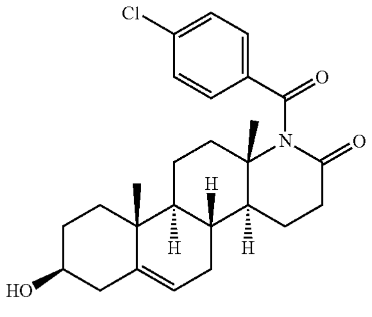

$^1$H NMR (500 MHz, $CDCl_3$) δ 7.66 (d, J=8.6 Hz, 2H), 7.34 (d, J=8.6 Hz, 2H), 5.33-5.32 (m, 1H), 3.46-3.40 (m, 1H), 2.54 (t, J=8.0 Hz, 2H), 2.28-2.13 (m, 5H), 2.02-1.98 (m, 1H), 1.79-1.55 (m, 6H), 1.51 (s, 3H), 1.48-1.22 (m, 5H), 1.10-0.97 (m, 2H), 0.94 (s, 3H).

$^{13}$C NMR (125 MHz, $CDCl_3$) δ 175.38, 173.42, 140.74, 139.22, 134.55, 130.26, 128.96, 120.62, 71.50, 61.84, 48.89, 48.65, 41.88, 36.91, 36.61, 35.89, 32.87, 32.07, 31.46, 31.41, 21.05, 20.99, 20.30, 19.21.

18. Compound (2)-5:

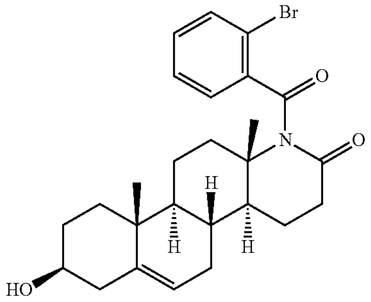

$^1$H NMR (400 MHz, $CDCl_3$) δ=7.53 (d, J=7.9 Hz, 1H), 7.47-7.45 (m, 1H), 7.31 (t, J=7.6 Hz, 1H), 7.24-7.19 (m, 1H), 5.37-5.35 (m, 1H), 3.56-3.48 (m, 1H), 2.77-2.72 (m, 1H), 2.58-2.53 (m, 2H), 2.35-2.18 (m, 3H), 2.02-1.96 (m 1H), 1.89-1.58 (m, 8H), 1.55 (s, 3H), 1.49-1.38 (m, 2H), 1.25 (s, 1H), 1.18-1.05 (m, 2H), 1.00 (s, 3H).

$^{13}$C NMR (100 MHz, $CDCl_3$) δ=174.38, 173.50, 140.88, 139.33, 133.76, 131.35, 129.83, 127.48, 120.72, 119.50, 71.61, 63.78, 48.91, 48.88, 41.94, 36.99, 36.70, 35.11, 33.26, 32.96, 31.62, 31.57, 21.54, 20.22, 20.15, 19.30.

19. Compound (2)-6:

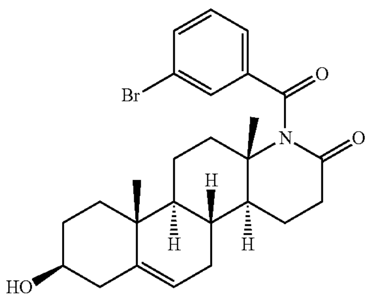

$^1$H NMR (500 MHz, $CDCl_3$) δ 7.68 (s, 1H), 7.47 (t, J=8.1 Hz, 2H), 7.12 (t, J=7.8 Hz, 1H), 5.19-5.18 (m, 1H), 3.30-3.23 (m, 1H), 2.46-2.32 (m, 2H), 2.10-1.86 (m, 5H), 1.65-1.59 (m, 2H), 1.54-1.42 (m, 4H), 1.35 (s, 3H), 1.26-1.13 (m, 3H), 1.06 (s, 2H), 0.96-0.87 (m, 2H), 0.80 (s, 3H).

$^{13}$C NMR (125 MHz, $CDCl_3$) δ 174.88, 174.18, 140.63, 137.53, 135.66, 131.44, 130.05, 127.26, 122.48, 120.23, 70.77, 62.03, 48.63, 48.18, 41.23, 36.71, 36.40, 35.66, 32.68, 31.53, 31.08, 30.74, 20.81, 20.59, 19.86, 18.80.

20. Compound (2)-7:

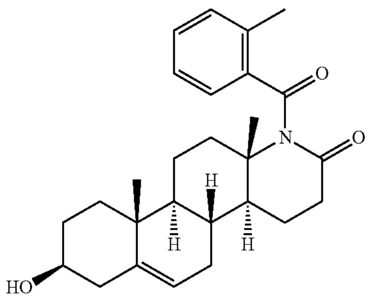

$^1$H NMR (400 MHz, $CDCl_3$) δ=7.39 (d, J=7.7 Hz, 1H), 7.31-7.27 (m, 1H), 7.21 (d, J=7.5 Hz, 1H), 7.14 (t, J=7.6 Hz,

1H), 5.36-5.34 (m, 1H), 3.50-3.42 (m, 1H), 2.54 (s, 3H), 2.49-2.43 (m, 3H), 2.31-2.15 (m, 4H), 2.01-1.95 (m, 1H), 1.85-1.76 (m, 2H), 1.72-1.56 (m, 4H), 1.54 (s, 3H), 1.51-1.36 (m, 4H), 1.17-1.01 (m, 2H), 0.97 (s, 3H).

$^{13}$C NMR (100 MHz, $CDCl_3$) δ 176.83, 173.87, 140.82, 139.12, 137.01, 131.69, 131.04, 127.60, 125.47, 120.55, 71.34, 61.94, 48.84, 48.73, 41.81, 36.91, 36.60, 35.55, 32.88, 32.56, 31.44, 31.38, 21.19, 20.83, 20.66, 20.34, 19.22.

21. Compound (2)-8:

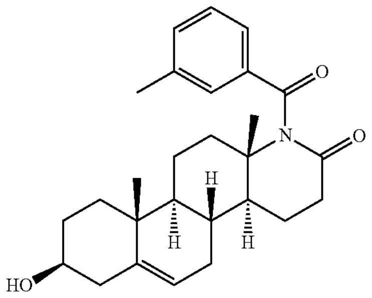

$^1$H NMR (400 MHz, $CDCl_3$) δ 7.59 (s, 1H), 7.53 (d, J=7.4 Hz, 1H), 7.32-7.27 (m, 2H), 5.35-5.34 (m, 1H), 3.50-3.42 (m, 1H), 2.63-2.52 (m, 2H), 2.36 (s, 3H), 2.31-2.16 (m, 5H), 2.04-1.99 (m, 1H), 1.82-1.57 (m, 6H), 1.53 (s, 3H), 1.47-1.24 (m, 4H), 1.14-1.01 (m, 2H), 0.96 (s, 3H).

$^{13}$C NMR (100 MHz, $CDCl_3$) δ 176.58, 173.30, 140.81, 138.44, 135.95, 133.84, 129.46, 128.49, 126.24, 120.57, 71.37, 61.56, 48.84, 48.48, 41.83, 36.90, 36.60, 35.83, 32.84, 31.95, 31.38, 29.72, 21.42, 21.11, 21.03, 20.33, 19.22.

22. Compound (2)-9:

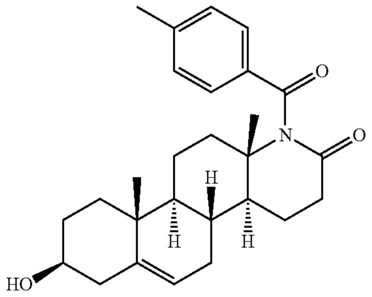

$^1$H NMR (500 MHz, $CDCl_3$) δ 7.68 (d, J=7.8 Hz, 2H), 7.20 (d, J=7.8 Hz, 2H), 5.37-5.36 (m, 1H), 3.52-3.46 (m, 1H), 2.61-2.52 (m, 2H), 2.37 (s, 1H), 2.33-2.15 (m, 4H), 2.04-2.00 (m, 1H), 1.84-1.58 (m, 8H), 1.54 (s, 1H), 1.38-1.25 (m, 3H), 1.13-1.00 (m, 2H), 0.97 (s, 2H).

$^{13}$C NMR (125 MHz, $CDCl_3$) δ 176.24, 173.12, 143.96, 140.81, 133.31, 129.44, 129.33, 120.69, 71.52, 61.46, 48.96, 48.59, 41.94, 36.97, 36.67, 35.96, 32.92, 31.94, 31.50, 31.47, 21.77, 21.21, 21.08, 20.41, 19.29.

23. Compound (2)-10:

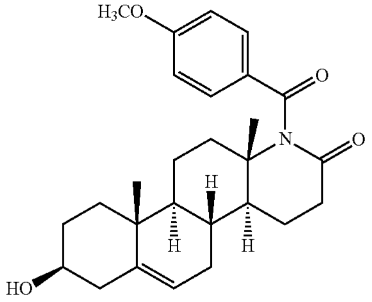

$^1$H NMR (500 MHz, $CDCl_3$) δ=7.78 (d, J=8.4 Hz, 2H), 6.90 (d, J=8.4 Hz, 2H), 3.84 (s, 3H), 3.62-3.55 (m, 1H), 2.58-2.55 (m, 2H), 2.11-2.04 (m, 2H), 1.99-1.95 (m, 1H), 1.79 (d, J=13.0 Hz, 1H), 1.64-1.58 (m, 6H), 1.52 (s, 3H), 1.32-1.25 (m, 7H), 0.99-0.84 (m, 4H), 0.78 (s, 3H).

$^{13}$C NMR (125 MHz, $CDCl_3$) δ=175.50, 172.89, 163.77, 131.83, 128.50, 114.07, 71.26, 61.55, 55.64, 53.22, 48.23, 44.38, 37.97, 36.86, 36.58, 36.44, 35.61, 31.65, 31.45, 30.96, 28.55, 21.33, 21.30, 20.29, 12.30.

24. Compound (2)-11:

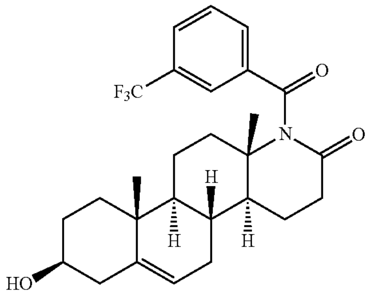

$^1$H NMR (500 MHz, $CDCl_3$) δ 7.98 (s, 1H), 7.88 (d, J=7.9 Hz, 1H), 7.74 (d, J=7.9 Hz, 1H), 7.53 (t, J=7.9 Hz, 1H), 5.38-5.37 (m, 1H), 3.53-3.47 (m, 1H), 2.60-2.53 (m, 2H), 2.34-2.19 (m, 4H), 2.07-2.03 (m, 1H), 1.84-1.61 (m, 7H), 1.56 (s, 3H), 1.51-1.25 (m, 4H), 1.16-1.03 (m, 2H), 0.99 (s, 3H).

$^{13}$C NMR (125 MHz, $CDCl_3$) δ 175.22, 173.89, 140.83, 137.14, 131.91, 131.30 (d, $J_{CF}$=32.7 Hz), 129.32, 129.17, 125.48 (d, $J_{CF}$=4.0 Hz), 124.83, 120.67, 71.56, 62.32, 48.91, 48.78, 41.96, 36.98, 36.70, 35.96, 32.95, 32.35, 31.54, 31.48, 21.19, 20.96, 20.38, 19.30.

25. Compound (2)-12:

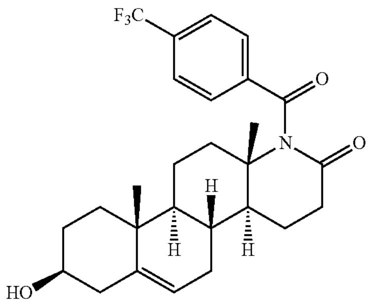

$^1H$ NMR (500 MHz, $CDCl_3$) δ 7.83 (d, J=8.0 Hz, 2H), 7.65 (d, J=8.1 Hz, 2H), 5.37-5.36 (m, 1H), 3.52-3.46 (m, 1H), 2.63-2.53 (m, 2H), 2.33-2.18 (m, 4H), 2.07-2.02 (m, 1H), 1.85-1.80 (m, 3H), 1.72-1.59 (m, 4H), 1.55 (s, 3H), 1.49-1.25 (m, 4H), 1.15-1.01 (m, 2H), 0.98 (s, 3H).

$^{13}C$ NMR (125 MHz, $CDCl_3$) δ 175.38, 173.92, 140.83, 139.48, 133.91 (d, $J_{CF}$=32.7 Hz), 128.91, 125.75 (q, $J_{CF}$=3.7 Hz), 124.78, 122.61, 120.62, 71.50, 62.32, 48.92, 48.79, 41.92, 36.97, 36.68, 35.90, 32.91, 32.36, 31.49, 21.18, 20.92, 20.32, 19.28.

26. Compound (2)-13:

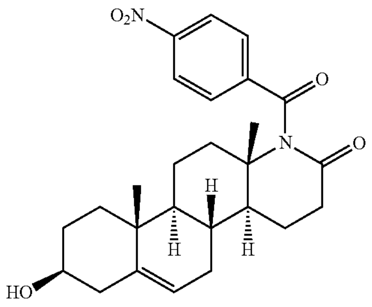

$^1H$ NMR (500 MHz, $CDCl_3$) δ 8.23 (d, J=8.2 Hz, 2H), 7.83 (d, J=8.3 Hz, 2H), 5.38-5.37 (m, 1H), 3.55-3.48 (m, 1H), 2.59-2.56 (m, 2H), 2.38-2.19 (m, 4H), 2.08-2.01 (m, 1H), 1.85-1.82 (m, 2H), 1.73-1.62 (m, 6H), 1.56 (s, 3H), 1.40-1.29 (m, 2H), 1.14-1.04 (m, 2H), 0.99 (s, 3H), 0.92-0.84 (m, 1H).

$^{13}C$ NMR (125 MHz, $CDCl_3$) δ 174.71, 174.23, 149.85, 141.94, 140.84, 129.25, 123.95, 120.64, 71.55, 62.74, 48.93, 48.91, 41.94, 37.00, 36.71, 35.90, 32.94, 32.58, 31.53, 29.81, 21.26, 20.76, 20.30, 19.31.

Example 3

Research on Biological Activities of Steroidal Piperidone Derivatives Against Aphids, Whiteflies, Rice Planthoppers, and Mites (1) Experiment on the Influence of Steroidal Piperidone Derivatives on the Activity of Aphids Inhibitory activities of the steroidal piperidone derivatives listed in Tables 1 and 2 against *Myzus persicae, Aphis citricola, Brevicoryne brassicae*, and wheat aphids were determined through slide-dip method. Specific process: A specified amount of a compound to be tested was accurately weighed and dissolved with acetone as a solvent, and solutions with concentrations of 50 μg/mL and 75 μg/mL were each prepared with a 0.1% Tween-80 aqueous solution, allowed to stand at room temperature for 0.5 h until the sample was completely dissolved, and stored for later use. Then, adult aphids were fixed with double-sided tape on slides with a small brush. One end of the slide with the aphids was immersed in the test solutions for 5 seconds. The excess liquid was absorbed with absorbent paper, and the mortality rates were calculated 24 h after treatment. Acetamiprid was adopted as a positive control, and a 0.1% Tween-80 aqueous solution was adopted as a negative control. and the results are shown in Table 1. $LC_{50}$ of inhibitory activity against *Aphis citricola* was tested, and results are shown in Table 2.

TABLE 1

Mortality of steroidal piperidone derivatives against aphid activity

| | Corrected mortality (%) | | | | | | | |
|---|---|---|---|---|---|---|---|---|
| | *Myzus persicae* | | *Aphis citricola* | | *Brevicoryne brassicae* | | Wheat aphid | |
| Compound | 75 μg/mL | 50 μg/mL | 75 μg/mL | 50 μg/mL | 75 μg/mL | 50 μg/mL | 75 μg/mL | 50 μg/mL |
| (1)-1 | 75.28 | 53.41 | 78.41 | 56.18 | 65.52 | 42.70 | 70.34 | 49.98 |
| (1)-2 | 55.06 | 26.14 | 61.36 | 39.33 | 54.02 | 30.34 | 50.36 | 22.09 |
| (1)-3 | 89.89 | 69.32 | 85.23 | 66.29 | 82.76 | 64.04 | 89.96 | 70.54 |
| (1)-4 | 100.00 | 84.09 | 100.00 | 89.89 | 100.00 | 86.52 | 100.00 | 91.02 |
| (1)-6 | 77.53 | 60.23 | 78.41 | 44.94 | 73.56 | 51.69 | 80.02 | 59.93 |
| (1)-11 | 52.81 | 25.00 | 54.55 | 25.84 | 50.57 | 24.72 | 56.45 | 30.42 |
| (1)-12 | 57.30 | 30.68 | 65.91 | 32.58 | 57.47 | 29.21 | 55.67 | 24.78 |
| (2)-7 | 100.00 | 93.18 | 100.00 | 92.13 | 100.00 | 94.38 | 100.00 | 96.04 |
| (2)-8 | 69.66 | 43.18 | 70.45 | 48.31 | 70.11 | 51.69 | 73.28 | 54.92 |
| (2)-9 | 100.00 | 80.68 | 100.00 | 88.76 | 100.00 | 78.65 | 100.00 | 85.45 |
| (2)-11 | 66.29 | 40.91 | 72.73 | 44.94 | 65.52 | 42.70 | 59.67 | 40.03 |
| (2)-12 | 79.78 | 59.09 | 82.95 | 60.67 | 82.76 | 61.80 | 84.32 | 65.03 |
| Acetamiprid | 100 | 94.32 | 100.00 | 93.26 | 100 | 94.38 | 100 | 95.47 |

TABLE 2

| LC$_{50}$ of inhibitory activities of steroidal piperidone derivatives against *Aphis citricola* | | | |
|---|---|---|---|
| Compound | Toxicity equation | Correlation coefficient (r) | LC$_{50}$ (μg/mL) |
| (1)-3 | y = 2.4629x + 1.8236 | 0.9813 | 24.6 |
| (1)-4 | y = 3.2757x + 1.5982 | 0.9924 | 11.9 |
| (2)-7 | y = 3.1231x + 1.8168 | 0.9877 | 10.3 |
| (2)-9 | y = 3.1644x + 1.5771 | 0.9965 | 14.2 |
| (2)-12 | y = 2.9779x + 1.5714 | 0.9992 | 21.9 |
| Acetamiprid | y = 3.1472x + 1.8522 | 0.9846 | 9.95 |

The laboratory bioassay results in Table 1 and Table 2 show that the test compounds exhibit excellent biological activities against *Myzus persicae, Aphis citricola, Brevicoryne brassicae*, and wheat aphids, and some compounds exhibit similar insecticidal effects to acetamiprid.

(2) Experiment on the Influence of Steroidal Piperidone Derivatives on the Activity of Mites The inhibitory activities of the steroidal piperidone derivatives listed in Table 3 on *Tetranychus truncatus* were tested through slide dipping. A specific process was the same as that of aphids, and the results are shown in Table 3.

TABLE 3

| Inhibitory activities of steroidal piperidone derivatives against *Tetranychus truncatus* Corrected mortality (%) | | |
|---|---|---|
| Compound | 75 μg/mL | 50 μg/mL |
| (1)-3 | 70.32 | 54.27 |
| (1)-4 | 88.64 | 64.23 |
| (1)-6 | 55.32 | 24.89 |
| (2)-5 | 69.63 | 43.55 |
| (2)-7 | 88.51 | 66.83 |
| (2)-8 | 54.43 | 30.32 |
| (2)-9 | 77.45 | 55.23 |
| (2)-12 | 55.47 | 33.82 |
| (2)-13 | 56.83 | 33.25 |
| Pyridaben | 89.34 | 65.29 |

The laboratory bioassay results in Table 3 show that the test compounds exhibit excellent biological activities against *Tetranychus truncatus*, and some compounds exhibit similar insecticidal effects to pyridaben.

(4) Experiment on the Influence of Steroidal Piperidone Derivatives on the Activity of *Bemisia tabaci*

The toxic activities of the steroidal piperidone derivatives listed in Table 4 against *B. tabaci* were tested by a foliar spray method. Specific process: A specified amount of a compound to be tested was accurately weighed and dissolved in acetone, and solutions with concentrations of 50 μg/mL and 75 μg/mL were each prepared with a 0.1% of Tween 80 aqueous solution and stored for later use. The pesticide solution was sprayed on the back side of a cucumber leaf, the cucumber leaf was naturally dried, and *B. tabaci* to be tested were placed on the cucumber leaf. Thiamethoxam was used as a positive control, and acetone was used as a negative control. Several deaths were observed after 7 d of treatment, and the corrected mortality was calculated. Results are shown in Table 3.

TABLE 4

| Inhibitory activities of steroidal piperidone derivatives against *B. tabaci* Corrected mortality (%) | | |
|---|---|---|
| Compound | 75 μg/mL | 50 μg/mL |
| (1)-3 | 74.71 | 67.73 |
| (1)-4 | 87.36 | 72.50 |
| (1)-6 | 67.47 | 56.14 |
| (2)-7 | 88.51 | 76.32 |
| (2)-8 | 56.32 | 31.82 |
| (2)-9 | 75.86 | 63.41 |
| (2)-10 | 69.08 | 48.55 |
| (2)-11 | 58.28 | 45.35 |
| (2)-12 | 58.62 | 47.50 |
| Thiamethoxam | 76.25 | 59.55 |

The indoor bioassay results in Table 4 show that the test compounds exhibit excellent biological activities against *B. tabaci*, and some compounds exhibit similar insecticidal effects to thiamethoxam.

(4) Experiment on the Influence of Steroidal Piperidone Derivatives on the Activity of Rice Planthoppers The toxic activities of the steroidal piperidone derivatives listed in Table 5 against rice planthoppers were tested by a foliar spray method. Imidacloprid was used as a positive control, and acetone was used as a negative control. Several deaths were observed after 3 d of treatment, and the corrected mortality was calculated. Results are shown in Table 5.

TABLE 5

| Insecticidal activities of steroidal piperidone derivatives against rice planthoppers Corrected mortality (%) | | |
|---|---|---|
| Compound | 75 μg/mL | 50 μg/mL |
| (1)-1 | 56.92 | 42.33 |
| (1)-2 | 60.28 | 52.11 |
| (1)-3 | 71.23 | 63.32 |
| (1)-4 | 80.43 | 72.02 |
| (1)-6 | 59.23 | 45.24 |
| (1)-7 | 45.78 | 36.25 |
| (1)-8 | 53.64 | 38.36 |
| (2)-7 | 79.25 | 64.17 |
| (2)-8 | 52.36 | 41.87 |
| (2)-9 | 66.24 | 59.58 |
| (2)-10 | 35.98 | 33.22 |
| (2)-11 | 57.83 | 35.33 |
| (2)-12 | 62.98 | 54.02 |
| Imidacloprid | 82.35 | 61.23 |

The laboratory bioassay results in Table 5 show that the test compounds exhibit excellent biological activities against rice planthoppers, and some compounds exhibit similar insecticidal effects to imidacloprid.

The foregoing description only provides preferred specific implementations of the present disclosure, and the protection scope of the present disclosure is not limited thereto. Any equivalent replacement or modification made by a person skilled in the art within the technical scope of the present disclosure according to the technical solution and inventive concept of the present disclosure shall fall within the protection scope of the present disclosure.

What is claimed is:

1. A steroidal piperidone derivative with a chemical structure shown in a general formula (1) or a general formula (2), (1)

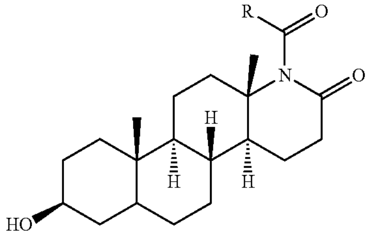

(2)

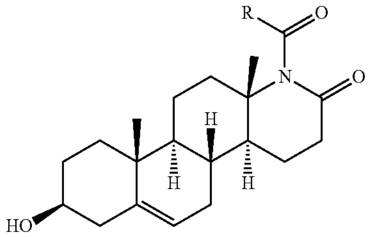

wherein R is (5g) or (6g):

(5g)

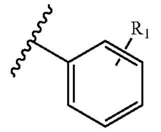

(6g)

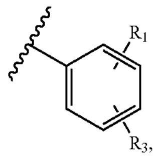

$R_1$ is a substituent at an ortho position, a meta position, or a para position;

$R_2$ and $R_3$ are each 2,3-substituted, 2,4-substituted, 2,5-substituted, 2,6-substituted, 3,4-substituted, 3,5-substituted, 3,6-substituted, 4,5-substituted, 4,6-substituted, or 5,6-substituted; and substituents of $R_1$, $R_2$, and $R_3$ are each one selected from the group consisting of halogen, trifluoromethyl, methyl, nitro, and methoxy.

2. The steroidal piperidone derivative according to claim 1, wherein the steroidal piperidone derivative has the following chemical structure:

(1)-1

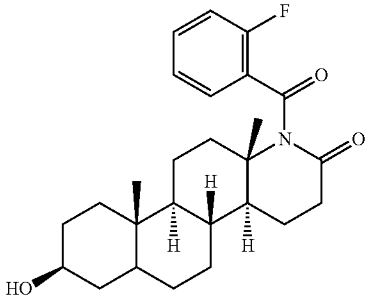

-continued (1)-2

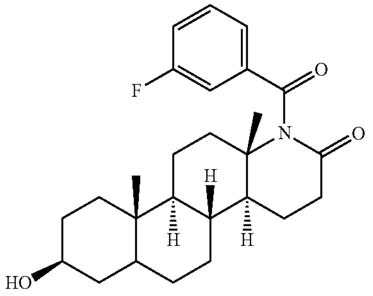

(1)-3

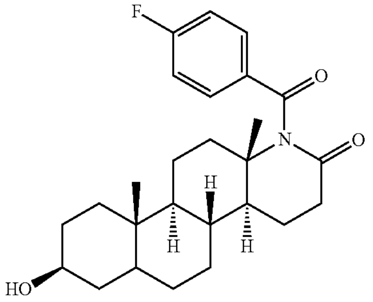

(1)-4

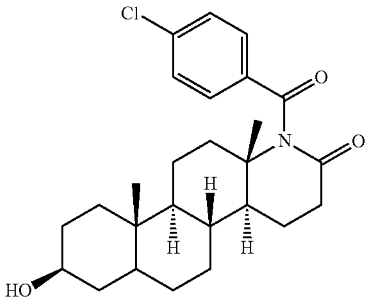

(1)-5

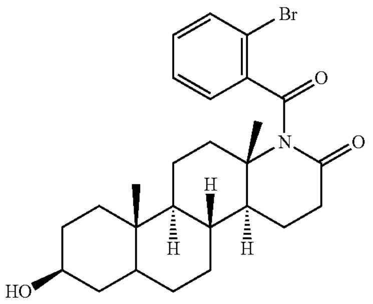

(1)-6

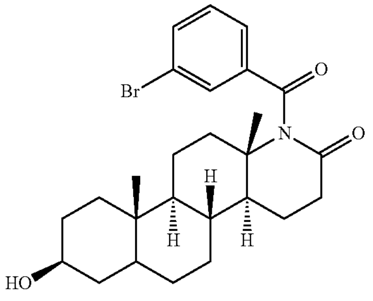

-continued
(1)-7
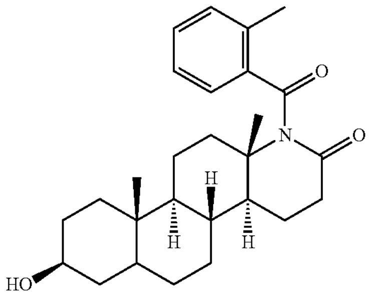
(1)-8
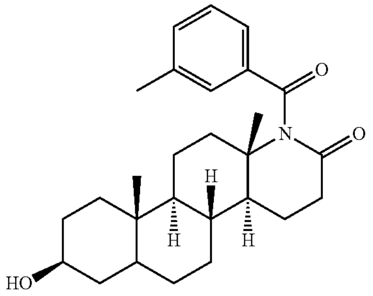
(1)-9
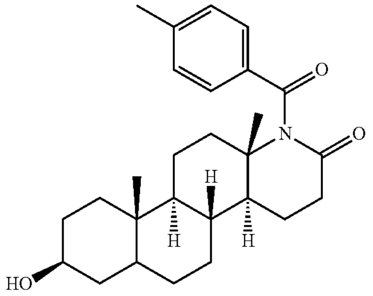
(1)-10
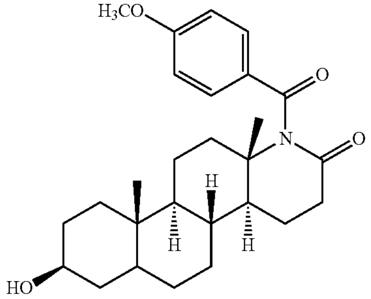
(1)-11
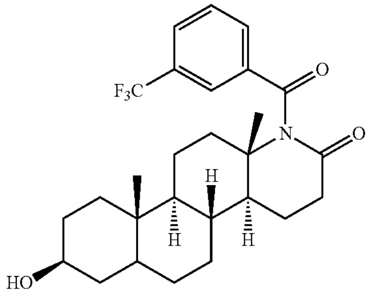
-continued
(1)-12
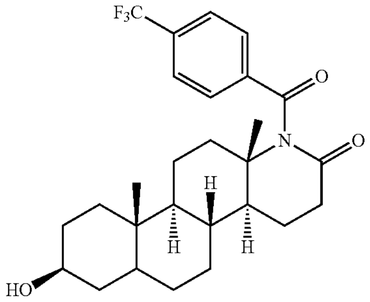
(1)-13
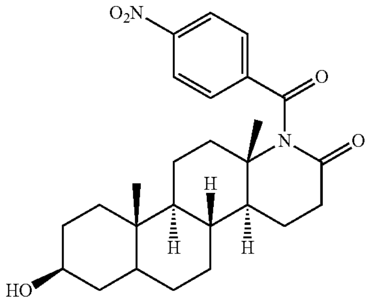
(2)-1
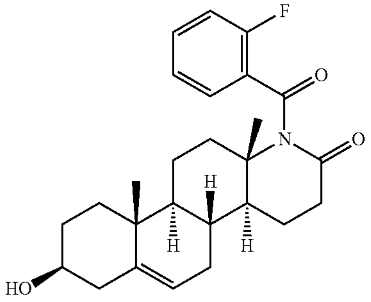
(2)-2
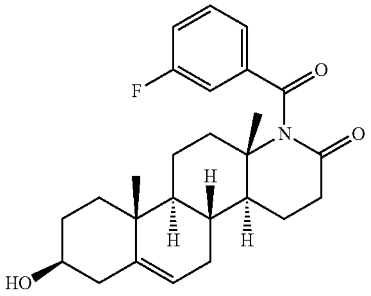
(2)-3
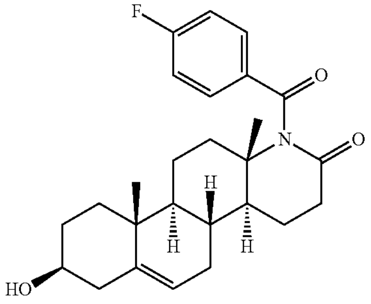

-continued
(2)-4
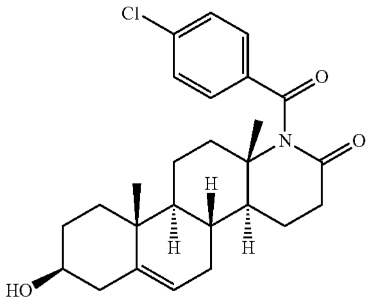
(2)-5
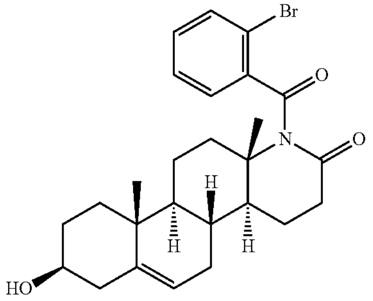
(2)-6
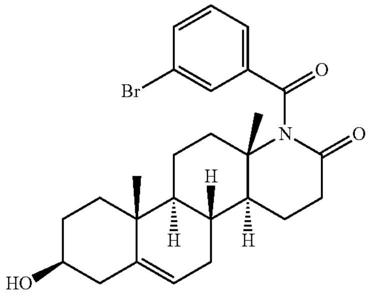
(2)-7
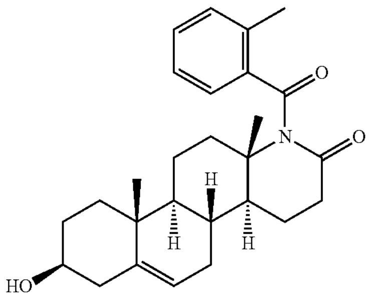
(2)-8
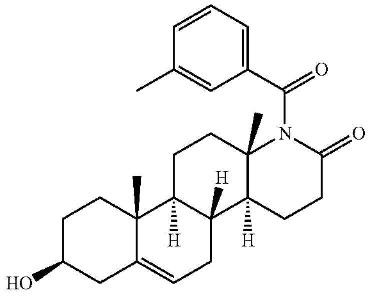
-continued
(2)-9
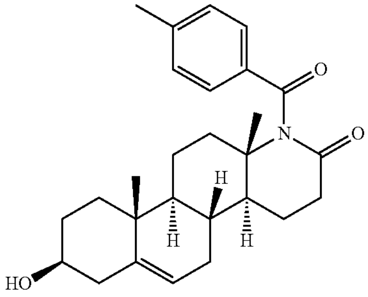
(2)-10
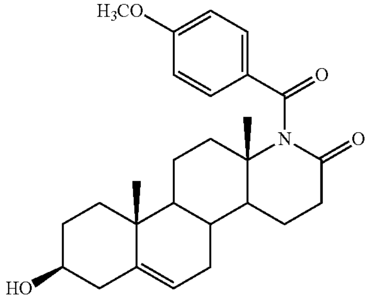
(2)-11
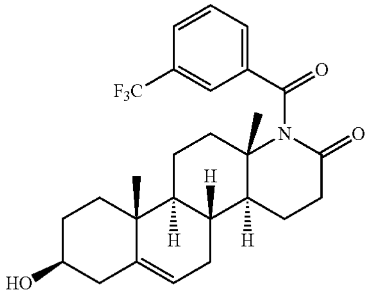
(2)-12
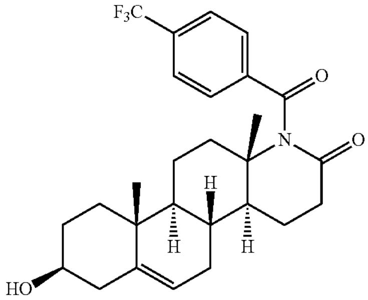
(2)-13
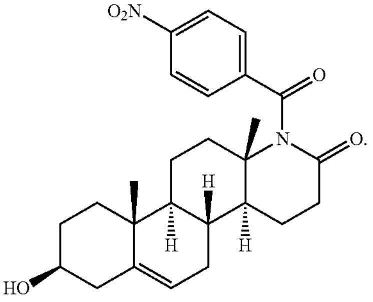
3. An insecticide prepared from the steroidal piperidone derivative according to claim 1.
4. The insecticide according to claim 3, wherein the steroidal piperidone derivative has the following chemical structure:

-continued
(1)-1
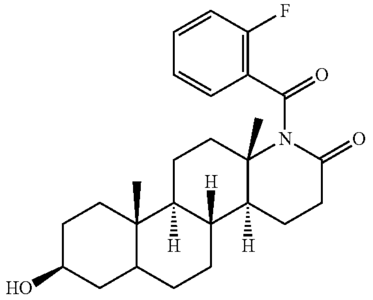
(1)-2
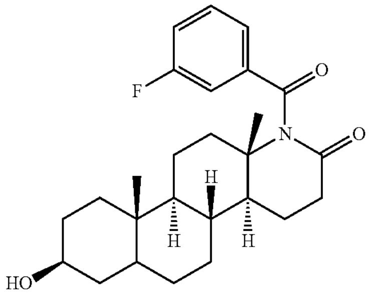
(1)-3
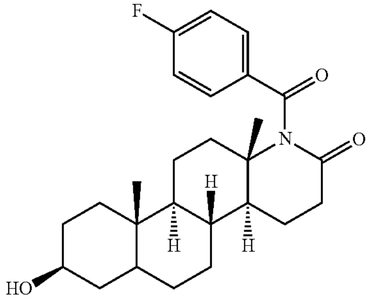
(1)-4
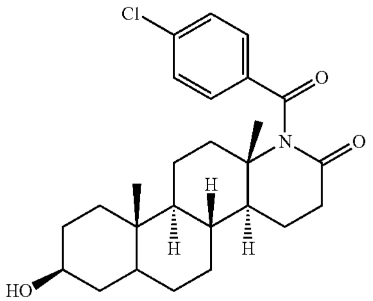
(1)-5
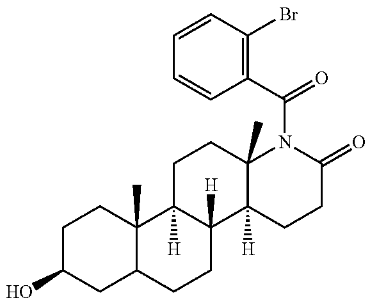
(1)-6
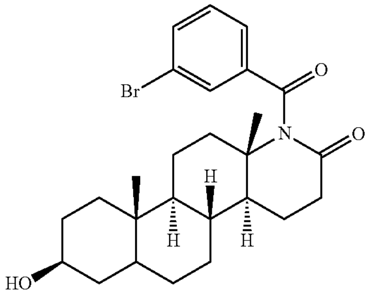
(1)-7
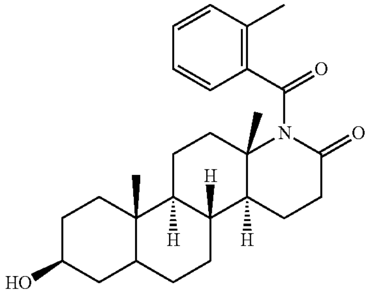
(1)-8
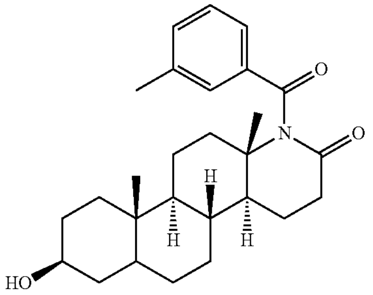
(1)-9
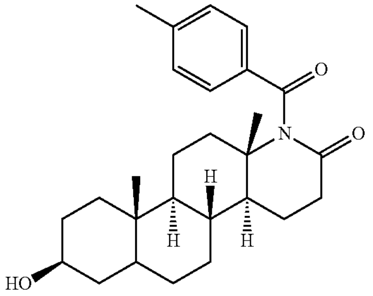
(1)-10
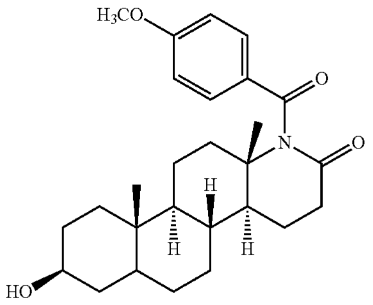

-continued
(1)-11
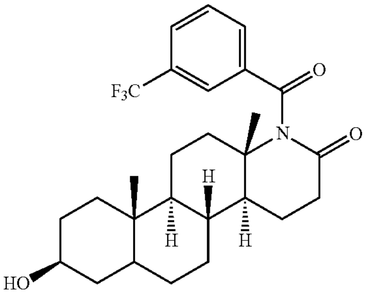
(1)-12
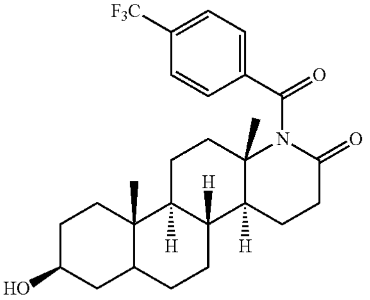
(1)-13
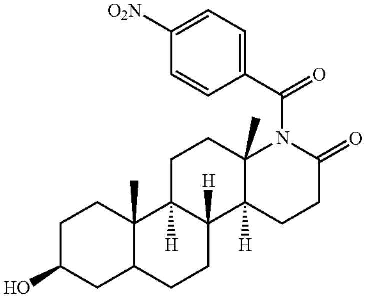
(2)-1
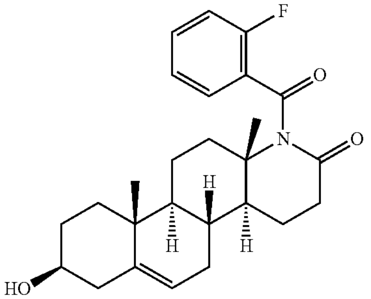
(2)-2
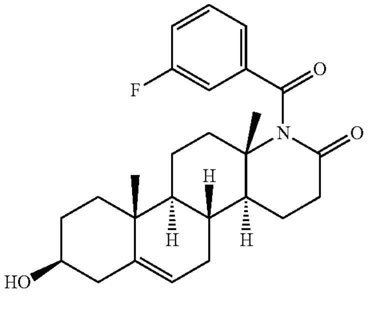
-continued
(2)-3
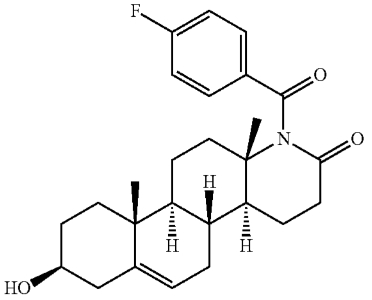
(2)-4
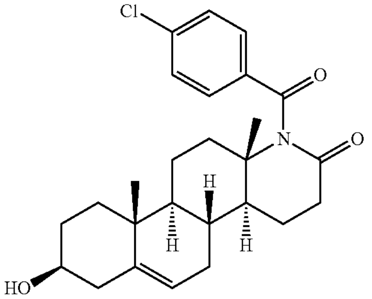
(2)-5
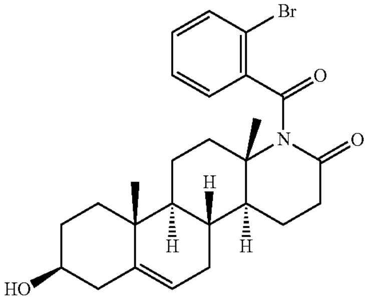
(2)-6
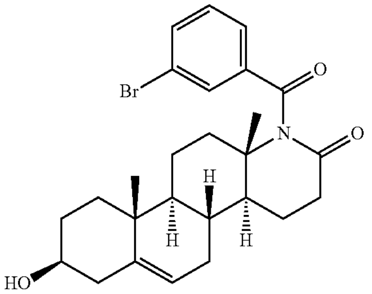
(2)-7
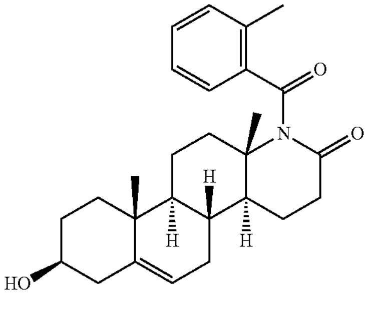

-continued
(2)-8
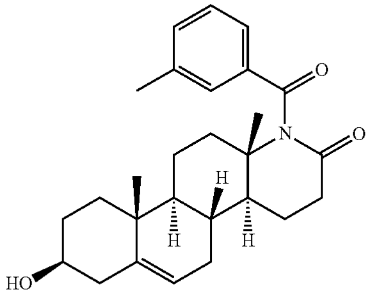
(2)-9
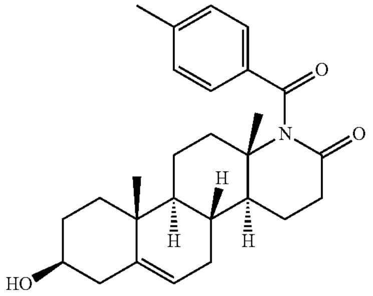
(2)-10
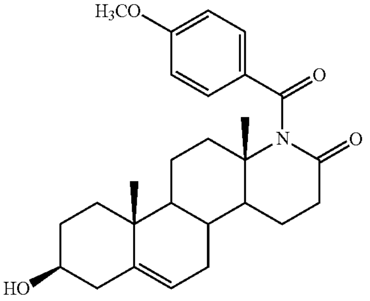
(2)-11
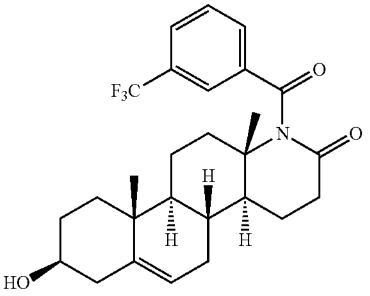
(2)-12
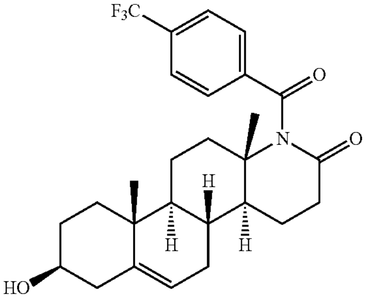
-continued
(2)-13
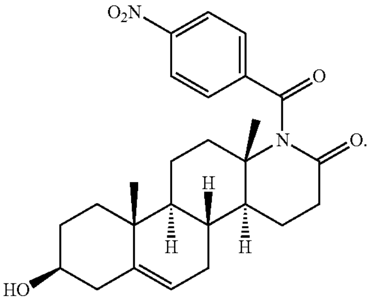
5. A method of controlling a plant pest, comprising applying the steroidal derivative according to claim 1 as a pesticide to a plant.
6. The method according to claim 5, wherein the plant pest is a sucking pest.
7. The method according to claim 5, wherein the steroidal piperidone derivative has the following chemical structure:
(1)-1
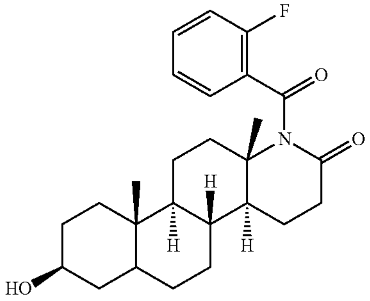
(1)-2
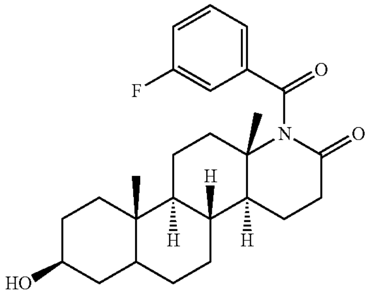
(1)-3
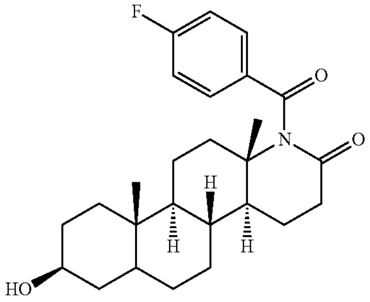

(1)-4
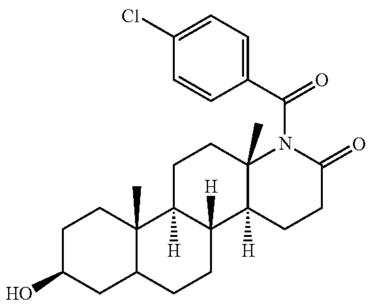
(1)-5
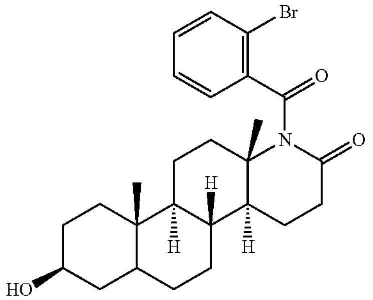
(1)-6
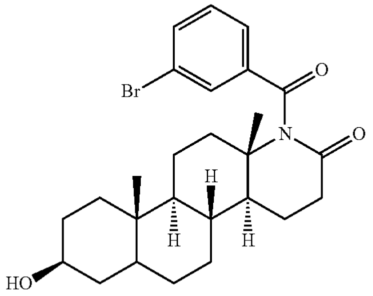
(1)-7
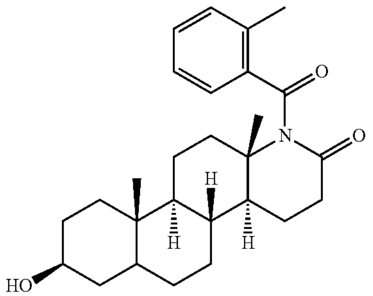
(1)-8
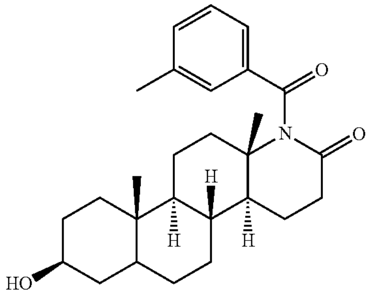
(1)-9
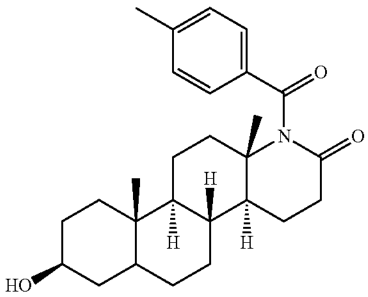
(1)-10
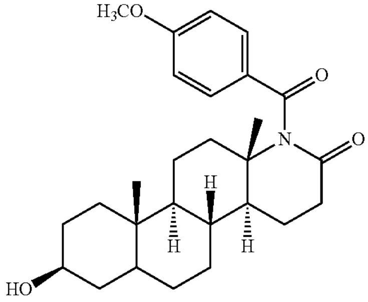
(1)-11
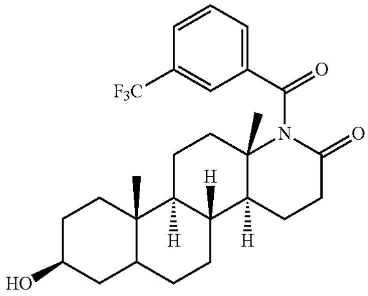
(1)-12
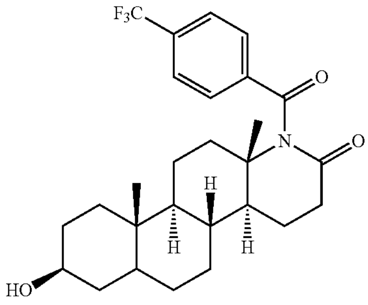
(1)-13
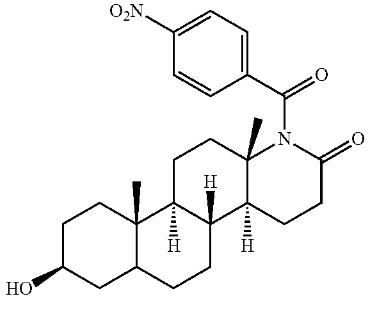

-continued
(2)-1
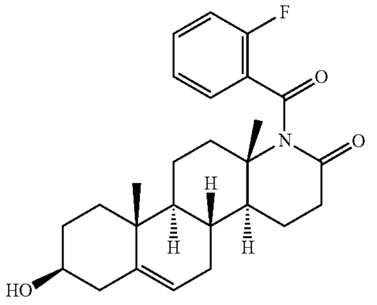
(2)-2
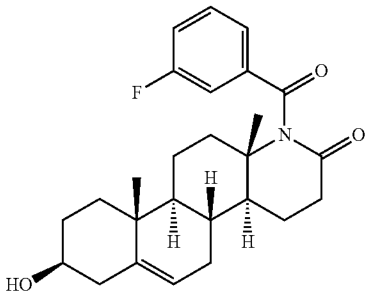
(2)-3
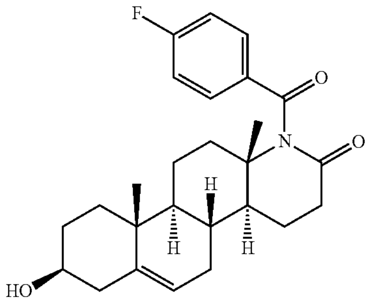
(2)-4
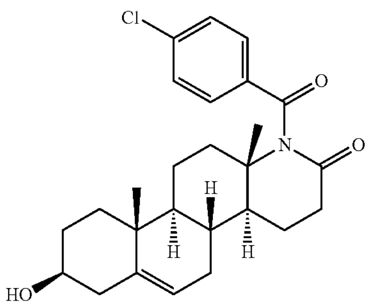
(2)-5
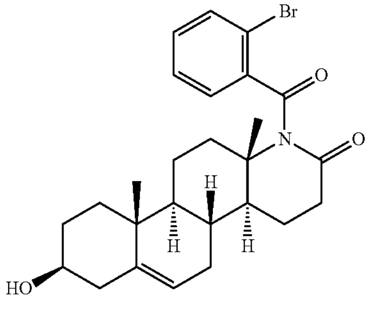
-continued
(2)-6
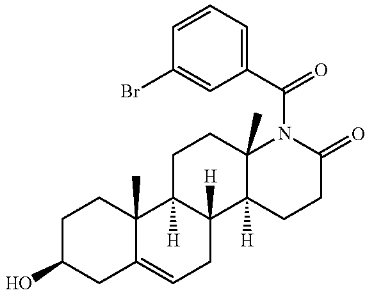
(2)-7
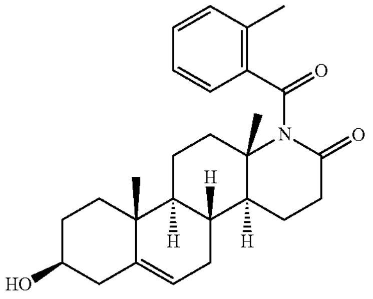
(2)-8
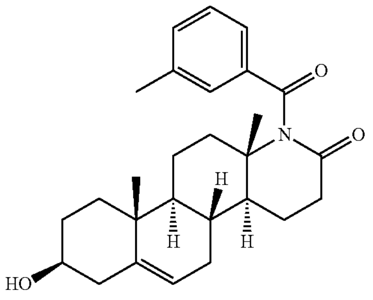
(2)-9
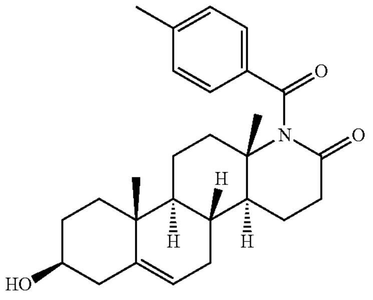
(2)-10
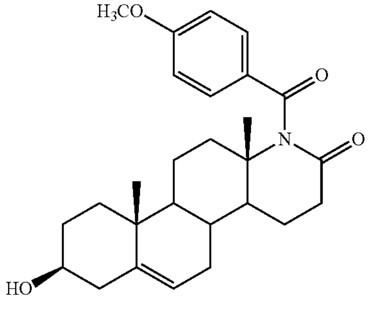

-continued (2)-11

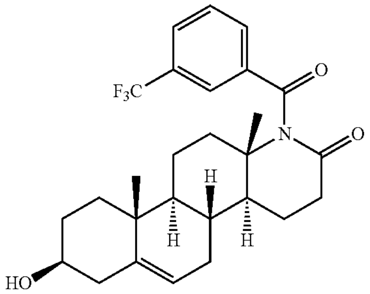

(2)-12

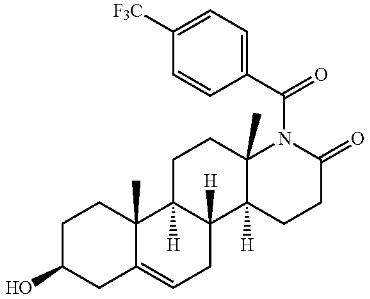

(2)-13

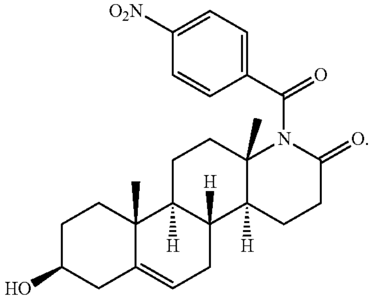

8. A synthesis method of the steroidal piperidone derivative according to claim 1, comprising the following synthetic routes:

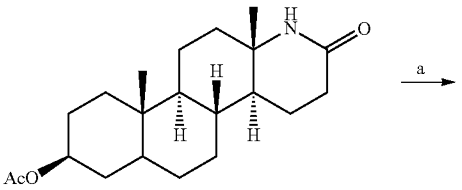

(3)

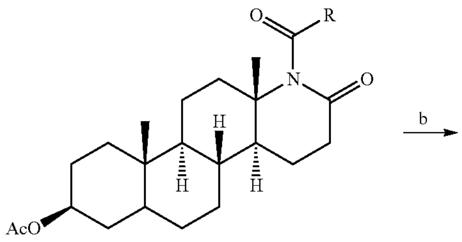

(4)

-continued

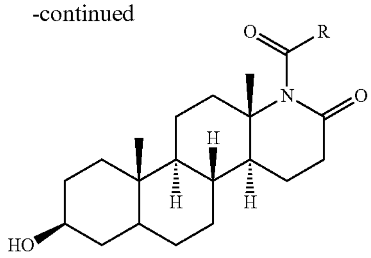

(1)

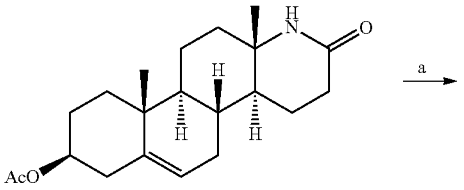

(5)

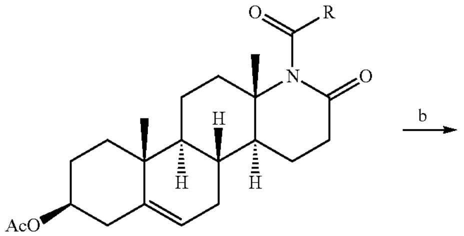

(6)

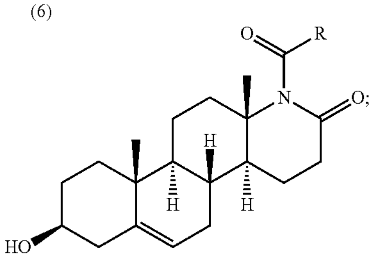

(2)

wherein step a is conducted as follows: adding 4-dimethylaminopyridine, triethylamine (TEA), and an acyl chloride with various substituents successively to dichloromethane (DCM), wherein the compound (3) or the compound (5) is dissolved in the DCM, and conducting a first reaction at room temperature for 6 h; and step b is conducted as follows: with methanol as a solvent, adding sodium carbonate, and conducting a second reaction under reflux for 2 h, wherein the various substituents are R, and R is (5g) or (6g):

(5g)

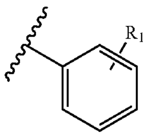

(6g)

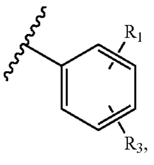

$R_1$ is a substituent at an ortho position, a meta position, or a para position;

$R_2$ and $R_3$ are each 2,3-substituted, 2,4-substituted, 2,5-substituted, 2,6-substituted, 3,4-substituted, 3,5-substituted, 3,6-substituted, 4,5-substituted, 4,6-substituted, or 5,6-substituted; and substituents of $R_1$, $R_2$, and $R_3$ are each one selected from the group consisting of halogen, trifluoromethyl, methyl, nitro, and methoxy.

9. The synthesis method of the steroidal piperidone derivative according to claim 8, wherein synthetic routes of the compound (5) and the compound (3) are as follows:

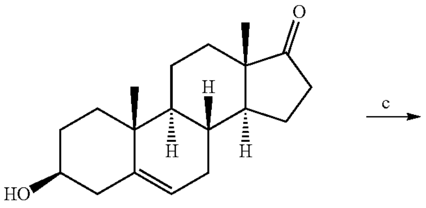

(7)

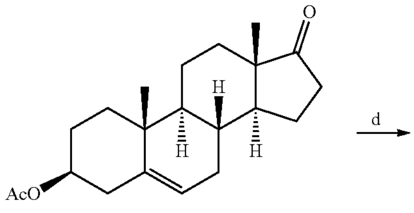

(8)

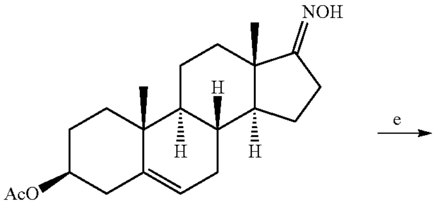

(9)

-continued

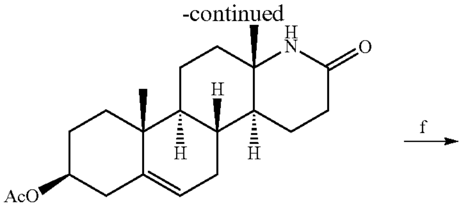

(5)

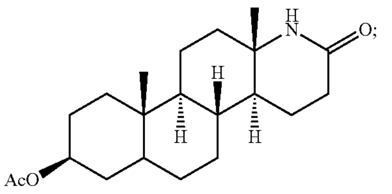

(3)

wherein step c is conducted as follows: adding acetic anhydride to a solution of the compound (7) in DCM, adding 4-dimethylaminopyridine and TEA, and conducting a third reaction at 25° C. for 2 h;

step d is conducted as follows: with ethanol as a solvent, adding the compound (8), hydroxylamine hydrochloride, and sodium acetate, and conducting a fourth reaction at room temperature for 0.5 h;

step e is conducted as follows: with tetrahydrofuran (THF) as a solvent, adding thionyl chloride, and conducting a fifth reaction at room temperature for 1 h; and step f is conducted as follows: with ethanol as a solvent and Pb/C as a catalyst, introducing hydrogen, and conducting a sixth reaction at room temperature for 60 h.

* * * * *